(12) United States Patent
Qiao et al.

(10) Patent No.: US 11,878,174 B2
(45) Date of Patent: Jan. 23, 2024

(54) IMPLANTABLE MEDICAL SYSTEMS AND METHODS USED TO DETECT, CHARACTERIZE OR AVOID ATRIAL OVERSENSING WITHIN A HIS IEGM

(71) Applicant: Pacesetter, Inc., Sylmar, CA (US)

(72) Inventors: Yun Qiao, Sunnyvale, CA (US); Wenwen Li, Studio City, CA (US); Jan Mangual, Rho (IT); Luke C. McSpadden, Studio City, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 17/171,762

(22) Filed: Feb. 9, 2021

(65) Prior Publication Data

US 2022/0249849 A1  Aug. 11, 2022

(51) Int. Cl.
 *A61N 1/37* (2006.01)
 *A61N 1/368* (2006.01)
 *A61N 1/05* (2006.01)
 *A61B 5/33* (2021.01)
 *A61B 5/283* (2021.01)

(52) U.S. Cl.
 CPC ............ *A61N 1/3714* (2013.01); *A61B 5/283* (2021.01); *A61B 5/33* (2021.01); *A61N 1/056* (2013.01); *A61N 1/3682* (2013.01); *A61N 1/3688* (2013.01)

(58) Field of Classification Search
 CPC .. A61N 1/3714; A61N 1/3688; A61N 1/3682; A61N 1/056; A61N 1/371
 See application file for complete search history.

(56) References Cited

U.S. PATENT DOCUMENTS

| 4,662,377 A | * | 5/1987 | Heilman | A61N 1/3956 607/4 |
| 5,601,615 A | | 2/1997 | Markowitz et al. | |
| 6,931,280 B1 | * | 8/2005 | Yang | A61N 1/36843 607/9 |
| 2016/0129261 A1 | * | 5/2016 | Demmer | A61N 1/3688 607/18 |
| 2019/0022378 A1 | | 1/2019 | Prillinger et al. | |

(Continued)

OTHER PUBLICATIONS

Saini, Aditya et al., "Novel Method for Assessment of HIS Bundle Pacing Morphology Using Near Field and Far Field Device Electrograms," Circulation: Arrhythmia and Electrophysiology, Feb. 2019, 11 pages.

(Continued)

*Primary Examiner* — William J Levicky
(74) *Attorney, Agent, or Firm* — Vierra Magen Marcus LLP

(57) ABSTRACT

Certain embodiments of the present technology described herein relate to detecting atrial oversensing in a His intracardiac electrogram (His IEGM), characterizing atrial oversensing, determining when atrial oversensing is likely to occur, and or reducing the chance of atrial oversensing occurring. Some such embodiments characterize and/or avoid atrial oversensing within a His IEGM. Other embodiments of the present technology described herein relate to determining whether atrial capture occurs in response to His bundle pacing (HBP). Still other embodiments of the present technology described herein relate to determining whether AV node capture occurs in response to HBP.

18 Claims, 18 Drawing Sheets

(56) References Cited

U.S. PATENT DOCUMENTS

| | | | |
|---|---|---|---|
| 2019/0134404 A1 | 5/2019 | Sheldon et al. | |
| 2019/0134405 A1 | 5/2019 | Sheldon et al. | |
| 2019/0192860 A1 | 6/2019 | Ghosh et al. | |
| 2019/0275329 A1 | 9/2019 | Brisben et al. | |
| 2019/0290918 A1 | 9/2019 | Ghosh | |
| 2020/0009390 A1 | 1/2020 | Casavant | |
| 2020/0330771 A1 | 10/2020 | Min | |
| 2020/0406041 A1 | 12/2020 | Cao et al. | |
| 2021/0052895 A1* | 2/2021 | Lybarger | A61N 1/3704 |

OTHER PUBLICATIONS

Burri, Harran, "His Bundle Pacing—Why Should You be Doing it?," European Journal of Arrhythmia & Electrophysiology, Sep. 2019, 5 pages.

U.S. Appl. No. 17/171,773, filed Feb. 9, 2021.

Notice of Allowance dated May 30, 2023, U.S. Appl. No. 17/171,773, filed Feb. 9, 2021.

Response to Office Action dated Feb. 1, 2023, U.S. Appl. No. 17/171,773, filed Feb. 9, 2021.

Non-final Office Action dated Nov. 7, 2022, U.S. Appl. No. 17/171,773, filed Feb. 9, 2021.

* cited by examiner

|  | His Bipolar | His Unipolar |
|---|---|---|
| With A oversensing | 31 ± 23 ms | 40 ± 26 ms |
| Without A oversensing | 234 ± 83 ms | 224 ± 84 ms |

Table 1. Summary of stim to onset interval of patients with and without atrial oversensing.

FIG. 9A

|  | AS-Onset | | AP-Onset | |
|---|---|---|---|---|
|  | His Bipolar | His Unipolar | His Bipolar | His Unipolar |
| With A oversensing | 24 ± 13 ms | 31 ± 12 ms | 74 ± 27 ms | 88 ± 34 ms |
| Without A oversensing | 230 ± 95 ms | 217 ± 95 ms | 242 ± 53 ms | 239 ± 57 ms |

Table 2. Summary of AS/AP to onset interval of patients with and without atrial oversensing.

FIG. 9B

IMPLANTABLE MEDICAL SYSTEMS AND METHODS USED TO DETECT, CHARACTERIZE OR AVOID ATRIAL OVERSENSING WITHIN A HIS IEGM

RELATED APPLICATION

The present application is related to commonly invented and commonly assigned U.S. patent application Ser. No. 17/171,773, filed the same day as the present application, titled IMPLANTABLE MEDICAL SYSTEMS AND METHODS FOR USE THEREWITH THAT DETECT ATRIAL CAPTURE AND AV NODE CAPTURE RESPONSIVE TO HIS BUNDLE PACING, which is incorporated herein by reference.

FIELD

This disclosure relates generally to implantable cardiac stimulating systems and/or devices for use in providing His bundle pacing (HBP), and related methods. More specifically, the present disclosure is directed to cardiac stimulation systems and/or devices for providing HBP and associated methods that perform, inter alia, atrial oversensing testing, atrial capture testing, and/or atrioventricular (AV) node capture testing.

BACKGROUND

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of His (also referred to as the His bundle, or more succinctly as the His), the left and right bundle branches, and the Purkinje fibers, causing depolarization and resulting contraction of the ventricular chamber. The depolarization of the interventricular septum and ventricles is generally referred to as a QRS complex and is observed by measuring electrical activity of the heart, such as by recording an intracardiac electrocardiogram (IEGM).

The His bundle (aka the His, or the bundle of His) is a narrow cluster of cardiac muscle fibers that passes electrical impulses from the AV node to the interventricular septum. It is anatomically located adjacent to the annulus of the tricuspid valve, inferior to or within the membranous septum. During normal functioning of the heart, the delay between excitation of the His bundle and a subsequent depolarization of the ventricles in response to the excitation is generally on the order of approximately 30-50 milliseconds (ms) and the resulting QRS complex generally has a duration of approximately 70-100 ms.

Disruption of the natural pacemaking and conduction system of the heart as a result of aging or disease can be successfully treated by artificial cardiac pacing using implantable cardiac stimulation devices, including pacemakers and implantable defibrillators. Such devices deliver rhythmic electrical impulses at particular energies and rates or provide other anti-arrhythmia therapies to the heart via electrodes implanted in contact with the heart tissue. To the extent the electrical impulses are sufficient to induce depolarization of the associated heart tissue, the heart tissue is said to be captured. The minimum electrical impulse energy resulting in capture is generally referred to as the capture threshold for the heart tissue.

In the majority of individuals, the most effective heartbeat is triggered by the patient's own natural pacing physiology. Implantable cardiac stimulation devices are intended to fill in when the natural pacing functionality of the patient's heart fails or acts inefficiently (such as in cases of sinus arrest and symptomatic bradycardia, respectively) or when the heart's conduction system fails or acts inefficiently (such as in cases of third-degree and second-degree (i.e., Mobitz II) AV blocks, respectively). In a large number of heart failure patients, natural conduction through the AV node and the His bundle are intact and disruption of ventricular rhythm is the result of conduction disorders residing in the left and/or right bundle branches.

Dilatation of the heart due to congestive heart failure (CHF) has been associated with delayed conduction through the ventricles. This delayed conduction leads to reduced hemodynamic efficiency of the failing heart because of the resulting poor synchronization of the heart chambers.

Direct stimulation of the His bundle has been found to provide hemodynamic improvement for various patients including those suffering from dilated cardiomyopathy but having otherwise normal ventricular activation. Other examples of patients that may benefit from direct stimulation of the His bundle include those with atrioventricular junction (AVJ) ablation or third-degree AV block, which may require permanent ventricular pacing. Accordingly, the natural conduction system, when intact, can provide hemodynamically optimal depolarization timing of the heart chambers.

Permanent His bundle pacing (HBP) has become increasingly popular as an alternative to right ventricular (RV) apical pacing for pacemaker patients or biventricular (BV) pacing for cardiac resynchronization therapy (CRT). The close proximity of the His bundle to the basal-septal atrial myocardium, AV node, and basal-septal ventricular myocardium presents unique challenges to medical personnel that perform implants, especially those new to His implants. AV node capture or simultaneous His and atrial capture may not be immediately apparent during an implant procedure without performing additional testing. In cases with successful His capture, the multi-signal components (one or more of atrial, His, and ventricular signal component) in a His IEGM could also disrupt implantable device logic and impair its normal functionality. For example, a large atrial signal component, if present on the His bipolar or unipolar IEGM, can cause atrial oversensing and have undesirable consequences. For example, where a device algorithm for automated measurement of His capture type and threshold relies on a bipolar and unipolar evoked response, such an algorithm may provide inaccurate results if atrial oversensing occurs. Additionally, a large atrial signal component or unintended atrial and AV node capture may cause unreliable sensing of the HBP evoked response, thus rendering the algorithm inaccurate.

BRIEF SUMMARY OF THE DISCLOSURE

Certain embodiments of the present technology described herein relate to detecting atrial oversensing in a His intracardiac electrogram (His IEGM), characterizing atrial oversensing, determining when atrial oversensing is likely to occur, and or reducing the chance of atrial oversensing occurring. Other embodiments of the present technology described herein relate to determining whether atrial capture occurs in response to His bundle pacing (HBP). Still other embodiments of the present technology described herein relate to determining whether AV node capture occurs in response to HBP.

Certain methods of the present technology relate to methods for use with an implantable medical system including one or more electrodes that can be used for sensing and pacing. One such method includes obtaining a His IEGM sensed using at least one electrode implanted in or proximate to a patient's His bundle; sensing or pacing a right atrium of the patient to thereby sense or pace an atrial event; determining whether a portion of the His IEGM exceeds a specified sense threshold within a specified window that begins an atrioventricular delay (AVD) following the sensed or paced atrial event; and detecting atrial oversensing based on results of the determining whether a portion of the His IEGM exceeds the specified sense threshold within the specified window. In accordance with an embodiment, the specified window, which begins the AVD following the sensed or paced atrial event, comprises an evoked response window. In such an embodiments, the determining whether a portion of the His IEGM exceeds the specified sense threshold within the specified window includes (at the AVD following the sensed or paced atrial event) triggering the evoked response window by delivering a subthreshold pacing pulse to a patient's His bundle using at least one electrode that is implanted in or proximate to the patient's His bundle, the subthreshold pacing pulse having energy below a capture threshold associated with the patient's His bundle and the right ventricular (RV) myocardium. The method can also include determining a first onset interval corresponding to a length of time between a beginning of the specified window and when the portion of the His IEGM exceeds the specified sense threshold within the specified window; sensing or pacing the right atrium of the patient to thereby sense or pace a further atrial event; determining whether a portion of the His IEGM exceeds the specified sense threshold within a further specified window that begins at an extended AVD following the further sensed or paced atrial event, wherein the extended AVD is equal to the specified AVD plus an extension interval that is less than the first onset interval; determining a second onset interval corresponding to a length of time between a beginning of the further specified window and when the portion of the His IEGM within the further specified window exceeds the specified sense threshold; determining whether the second onset interval is equal to the first onset interval minus the extension interval; and detecting atrial oversensing in response to determining that the second onset interval is equal to the first onset interval minus the extension interval. The method can also include preventing performance of His capture management in response to detecting atrial oversensing, and after detecting atrial oversensing, at a later point in time that atrial oversensing is no longer detected, enabling performance of the His capture management.

Certain embodiments of the present technology relate to a medical system comprising: one or more implantable electrodes that can be used for sensing and pacing a patient's His bundle; a sensing circuit configured to sense a His IEGM using at least one said electrode that is implanted in or proximate to the patient's His bundle; a pulse generator configured to selectively produce pacing pulses that are delivered to the patient's His bundle using at least one said electrode that is implanted in or proximate to the patient's His bundle; and a controller. In accordance with certain embodiments, the controller is configured to: determine whether a portion of the His IEGM exceeds a specified sense threshold within a specified window that begins an AVD following the sensed or paced atrial event; and detect atrial oversensing based on results of the determining whether a portion of the His IEGM exceeds the specified sense threshold within the specified window. In certain embodiments, the specified window, which begins the AVD following the sensed or paced atrial event, comprises an evoked response window; and the controller (in order to determine whether a portion of the His IEGM exceeds the specified sense threshold within the specified window that begins the AVD following the sensed or paced atrial event) is configured to (at the AVD following the sensed or paced atrial event) trigger the evoked response window by causing delivery of a subthreshold pacing pulse to a patient's His bundle using at least one electrode that is implanted in or proximate to the patient's His bundle, the subthreshold pacing pulse having energy below a capture threshold associated with the patient's His bundle and the RV myocardium. Additional features and/or functions of the controller can be appreciated from the above portion of this summary, and the detailed description set forth below.

Another method of the present technology comprises: obtaining a His IEGM sensed using at least one electrode implanted in or proximate to a patient's His bundle; sensing or pacing a right atrium of the patient to thereby sense or pace an atrial event; determining whether a portion of the His IEGM exceeds a specified sense threshold within a specified window within an AVD following the sensed or paced atrial event; and detecting an atrial signal component within the His IEGM based on results of the determining whether a portion of the His IEGM exceeds the specified sense threshold within the specified window within the AVD. In such an embodiment, detecting an atrial signal component within the His IEGM is indicative of potential atrial oversensing. In certain embodiments, the AVD is long enough to allow for intrinsic atrioventricular conduction within the AVD; and the method is performed while the implantable medical system is in one of DDT or DDD mode. In one embodiment, the method is performed while the implantable medical system is in DDT mode, and the method further comprises triggering ventricular pacing in response to detecting a portion of the His IEGM exceeding the specified sense threshold within the AVD, or at the end of the AVD if no portion of the His IEGM exceeds the specified sense threshold within the AVD.

In certain embodiments, in response to detecting an atrial signal component within the His IEGM, the obtaining, pacing, and determining are repeated one or more time(s) to confirm the detecting of an atrial signal component within the His IEGM. In certain embodiments, in response to detecting an atrial signal component within the His IEGM, or confirmation thereof, the method further comprises: determining an atrial event-to-threshold crossing interval corresponding to a length of time between a paced or sensed atrial event and a respective crossing of the specified sense threshold; and specifying an atrial oversensing avoidance (AOA) period based on the atrial event-to-threshold crossing interval, the AOA period corresponding to when atrial oversensing may occur following paced or sensed atrial events. A method can also comprise, after specifying the AOA period: determining that a portion of the His IEGM within the AOA period exceeds a specified sense threshold, detecting a peak amplitude of the portion of the His IEGM that exceeds the specified sense threshold within the AOA period; detecting a peak of a portion of the His IEGM, following the AOA period, that corresponds to a ventricular depolarization; determining a ratio of the peak amplitude within the AOA period to the peak amplitude following the AOA period; determining whether the determined ratio exceeds specified ratio threshold; and determining that an atrial oversensing avoidance technique is to be used in response to determining that the determined ratio exceeds the specified ratio threshold. In accordance with an embodiment, after specifying the AOA period, and while the implantable medical system is in DDD mode, the method also includes: sensing or pacing the right atrium of the patient to thereby sense or pace an atrial event; and determining whether a portion of the His IEGM exceeds a multi-level sense threshold within a specified window that begins following the sensed or paced atrial event; wherein the multi-level sense threshold is greater during each said AOA period than following each said AOA period.

A medical system, according to an embodiment of the present technology, comprises: one or more implantable electrodes that can be used for sensing and pacing a patient's His bundle; a sensing circuit configured to sense a His IEGM using at least one said electrode that is implanted in or proximate to the patient's His bundle; a pulse generator configured to selectively produce pacing pulses that are delivered to the patient's His bundle using at least one said electrode that is implanted in or proximate to the patient's His bundle; and a controller. The controller is configured to: cause sensing or pacing of the right atrium of the patient to thereby sense or pace an atrial event; determine whether a portion of the His IEGM exceeds a specified sense threshold within a specified window within an AVD following the sensed or paced atrial event; and detect an atrial signal component within the His IEGM based on whether it is determined that a portion of the His IEGM exceeds the specified sense threshold within the specified window within the AVD. In certain embodiments, the controller is also configured to: determine an atrial event-to-threshold crossing interval corresponding to a length of time between a paced or sensed atrial event and a respective crossing of the specified sense threshold within the specified window within the AVD; specify an atrial oversensing avoidance (AOA) period based on the atrial event-to-threshold crossing interval, the AOA period corresponding to when atrial oversensing may occur following paced or sensed atrial events; detect a peak amplitude of a portion of the His IEGM that exceeds the specified sense threshold within the AOA period; detect a peak of a portion of the His IEGM, following the AOA period, that corresponds to a ventricular depolarization; determine a ratio of the peak amplitude within the AOA period to the peak amplitude following the AOA period; determine whether the determined ratio exceeds specified ratio threshold; and determine that an atrial oversensing avoidance technique is to be used in response to determining that the determined ratio exceeds the specified ratio threshold. The controller can also be configured to: determine whether a portion of the His IEGM exceeds a multi-level sense threshold within a specified window that begins following a sensed or paced atrial event; wherein the multi-level sense threshold is greater during each said AOA period than following each said AOA period.

Certain embodiments of the present technology relate to a method for performing an atrial capture test that can be used to detect if and/or when atrial capture occurs in response to pacing a patient's His bundle using at least one electrode that is implanted in or proximate to the patient's His bundle. Such a method comprises: during a plurality of cardiac cycles during which pacing of a patient's His bundle occurs using at least one electrode implanted in or proximate to a patient's His bundle, gradually decremented over time amplitudes of pacing pulses that are delivered to the patient's His bundle until loss of His or RV myocardium capture occurs, such that the patient's His bundle is paced at a plurality of different pacing pulse amplitudes; for each pacing pulse amplitude, of the different pacing pulse amplitudes used during the pacing of the patient's His bundle, determining a respective stimulation-to-atrial sense (stim-to-AS) interval corresponding to a length of time between when a said His pacing pulse having the pacing pulse amplitude is delivered and when a respective atrial sensed event occurs; detecting how many increases to the stim-to-AS interval occurred, if any, in response to the pacing pulse amplitudes being gradually decremented over time until the loss of His or RV myocardium capture occurs; and determining whether atrial capture occurred, during the pacing of the patient's His bundle, based on results of the detecting how many increases to the stim-to-AS interval occurred, if any. If one or more increases to the stim-to-AS interval are detected, the method also includes identifying a corresponding pacing pulse amplitude at which each of the one or more increases to the stim-to-AS interval occurred, and the determining whether atrial capture occurred is also based on the corresponding pacing pulse amplitude at which at least one of the one or more increases to the stim-to-AS interval occurred. The method can also include determining that atrial capture occurred and that an atrial capture threshold is below a capture threshold of the His bundle, if there were zero detected increases to the stim-to-AS interval in response to the pacing pulse amplitudes being gradually decremented over time until the loss of His or RV myocardium capture occurs. In accordance with certain embodiments, after determining that atrial capture occurred, the method further comprises: determining an atrial capture threshold; and selecting a pacing pulse amplitude, at which to perform further pacing of the patient's His bundle, that is below the atrial capture threshold and above the amplitude at which loss of His or RV myocardium capture occurs. Additional details of this method are described below in the detailed description. The above summarized method can be used during an implant procedure to help select a location for chronic implant of a lead and/or electrode that is to be used for pacing of the patient's His bundle.

A medical system, according to an embodiment of the present technology, comprises: one or more implantable electrodes that can be used for sensing and pacing; a sensing circuit configured to sense a His IEGM using at least one said electrode that is implanted in or proximate to a patient's His bundle; a pulse generator configured to selectively produce pacing pulses that are delivered to the patient's His bundle using at least one said electrode that is implanted in or proximate to the patient's His bundle; and a controller. The controller is configured to: cause gradual decrementing over time of amplitudes of pacing pulses that are delivered to the patient's His bundle until loss of His or RV myocardium capture occurs, such that the patient's His bundle is paced at a plurality of different pacing pulse amplitudes; for each pacing pulse amplitude, of the different pacing pulse amplitudes used during the pacing of the patient's His bundle, determine a respective stim-to-AS interval corresponding to a length of time between when a said His pacing pulse having the pacing pulse amplitude is delivered and when a respective atrial sensed event occurs; detect how many increases to the stim-to-AS interval occurred, if any, in response to the pacing pulse amplitudes being gradually decremented over time until the loss of His or RV myocardium capture occurs; and determine whether atrial capture occurred, during the pacing of the patient's His bundle, based on results of the detecting how many increases to the stim-to-AS interval occurred, if any. The controller can also be configured to: identify a corresponding pacing pulse amplitude at which each of the one or more increases to the stim-to-AS interval occurred, if one or more increases to the stim-to-AS interval are detected; and determine whether atrial capture occurred, during the pacing of the patient's His bundle, also based on the corresponding pacing pulse amplitude at which at least one of the one or more increases to the stim-to-AS interval occurred. The controller can further be configured to: determine that atrial capture occurred and that an atrial capture threshold is below a capture threshold of the His bundle if there were zero detected increases to the stim-to-AS interval in response to the pacing pulse amplitudes being gradually decremented over time until the loss of His or RV myocardium capture occurs. In accordance with certain embodiments, the controller is also configured to: determine an atrial capture threshold if atrial capture occurred; and select a pacing pulse amplitude, at which to perform further pacing of the patient's His bundle, that is below the atrial capture threshold and above the amplitude at which loss of His or RV myocardium capture occurs. Additional features and/or functions of the controller can be appreciated from the above portion of this summary, and the detailed description set forth below.

Certain methods of the present technology relate to methods for use with an implantable medical system including one or more electrodes that can be used for sensing and pacing. One such method includes obtaining a His IEGM sensed using at least one electrode implanted in or proximate to a patient's His bundle; for each of a plurality of cardiac cycles during which the His IEGM is obtained, sensing or pacing a right atrium of the patient to thereby sense or pace an atrial event, pacing the patient's His bundle at a shortened AVD following the sensed or paced atrial event, and determining whether a portion of the His IEGM exceeds a specified sense threshold within a specified window that begins the shortened AVD following the sensed or paced atrial event. The method also includes determining whether AV node capture occurred based on results of the determining whether a portion of the His IEGM exceeds the specified sense threshold within the specified window. In accordance with certain embodiments, the specified window, which begins the shortened AVD following the sensed or paced atrial event, comprises an evoked response window; and the pacing the patient's His bundle at the shortened AVD following the sensed or paced atrial event comprises, (at the shortened AVD following the sensed or paced atrial event) triggering the evoked response window by delivering a pacing pulse to a patient's His bundle using at least one electrode that is implanted in or proximate to the patient's His bundle, the pacing pulse having energy above a capture threshold associated with the patient's His bundle or the RV myocardium. The method can include determining that AV node capture did occur, in response to determining that a portion of the His IEGM did not exceed the specified sense threshold within the specified window that begins the shortened AVD following the sensed or paced atrial event. In accordance with certain embodiments, in response to determining that a portion of the His IEGM did exceed the specified sense threshold within the specified window that begins the shortened AVD following the sensed or paced atrial event, then determining that one of AV node capture or His bundle capture occurred, and distinguishing between AV node capture and His bundle capture. In accordance with certain embodiments, the distinguishing between AV node capture and His bundle capture is achieved by performing the following: during a further plurality of cardiac cycles during which pacing of the patient's His bundle occurs using the at least one electrode implanted in or proximate to a patient's His bundle, gradually decrementing over time a His bundle cycle length pacing interval, determining whether stimulation-to-onset intervals progressively increased in response to the gradually decrementing over time the His bundle cycle length pacing interval, and determining that AV node capture occurred, in response to determining that the stimulation-to-onset intervals progressively increased in response to the gradually decrementing over time the His bundle cycle length pacing interval. If the stimulation-to-onset intervals did not progressively increase in response to the gradually decrementing over time the His bundle cycle length pacing interval, then it would have been determined that His bundle capture occurred without AV node capture. The aforementioned method can be used during an implant procedure to help select a location for chronic implant of a lead and/or electrode that is to be used for pacing of the patient's His bundle, and the lead and/or electrode can be repositioned if AV node capture is detected.

A medical system, according to an embodiment of the present technology, comprises: one or more implantable electrodes that can be used for sensing and pacing; a sensing circuit configured to sense a His IEGM using at least one said electrode that is implanted in or proximate to a patient's His bundle; a pulse generator configured to selectively produce pacing pulses that are delivered to the patient's His bundle using at least one said electrode that is implanted in or proximate to the patient's His bundle; and a controller. The controller is configured to: cause sensing or pacing of a right atrium of the patient to thereby sense or pace an atrial event for each of a plurality of cardiac cycles during which an IEGM is being sensed using at least one electrode implanted in or proximate to a patient's His bundle. The controller is also configured to cause pacing of the patient's His bundle at a shortened AVD following the sensed or paced atrial event; determine whether a portion of the His IEGM exceeds a specified sense threshold within a specified window that begins the shortened AVD following the sensed or paced atrial event; and determine whether AV node capture occurred based on whether a portion of the His IEGM exceeds the specified sense threshold within the specified window. In accordance with certain embodiments, the controller is configured to determine that AV node capture did occur, in response to determining that a portion of the His IEGM did not exceed the specified sense threshold within the specified window that begins the shortened AVD following the sensed or paced atrial event. In accordance with certain embodiments, the controller is configured to: determine that one of AV node capture or His bundle capture occurred in response to determining that a portion of the His IEGM did exceed the specified sense threshold within the specified window that begins the shortened AVD following the sensed or paced atrial event, and distinguish between AV node capture and His bundle capture. The controller can be configured to distinguish between AV node capture and His bundle capture by performing the following: during a further plurality of cardiac cycles during which pacing of the patient's His bundle occurs using the at least one electrode implanted in or proximate to a patient's His bundle, causing a gradually decrementing over time a His bundle cycle length pacing interval; determine whether stimulation-to-onset intervals progressively increased in response to the gradually decrementing over time the His bundle cycle length pacing interval; and determine that AV node capture occurred, in response to determining that the stimulation-to-onset intervals progressively increased in response to the gradually decrementing over time the His bundle cycle length pacing interval. The controller can also be configured to determine that His bundle capture occurred without AV node capture, in response to determining that the stimulation-to-onset intervals did not progressively increase in response to the gradually decrementing over time the His bundle cycle length pacing interval.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

The various features of the present disclosure and the manner of attaining them will be described in greater detail with reference to the following description, claims, and drawings, wherein reference numerals are reused, where appropriate, to indicate a correspondence between the referenced items, and wherein:

FIG. 9A includes a table that summarizes stim-to-onset intervals of patient's with and without oversensing, which table can be used to specify the length of the specified window used with the atrial oversensing test summarized with reference to FIGS. 5 and 6.

FIG. 9B includes a table that summarizes AS/AP to onset intervals of patient's with and without oversensing, which table can be used to specify the length of the specified window used with the atrial oversensing test summarized with reference to FIG. 7.

DETAILED DESCRIPTION

Figure 1:
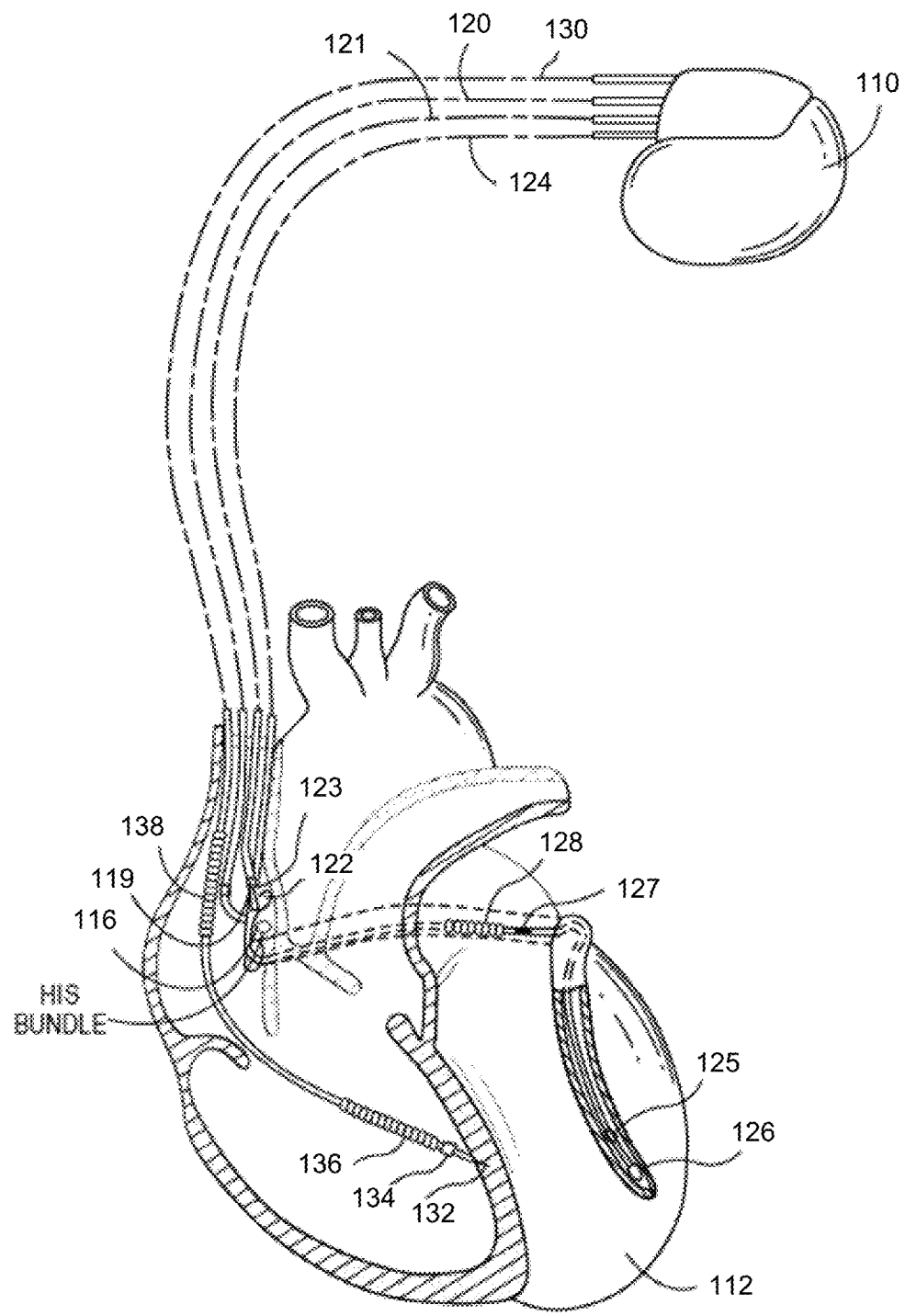
FIG. 1 is a simplified, partly cutaway view illustrating an implantable stimulation device in electrical communication with multiple leads, including a His bundle lead, implanted into a patient's heart for delivering multi-chamber stimulation and shock therapy.

The present disclosure is directed to various aspects of stimulation devices and corresponding methods related to His bundle pacing (HBP). Among other things, the present disclosure provides methods and devices for performing atrial oversensing, atrial capture, and AV node capture testing. Aspects of the present disclosure may be implemented in any suitable stimulation device including, but not limited to, implantable dual chamber and multi-chamber cardiac stimulation devices as well as external programming units for such stimulation devices. For example, the present disclosure may be implemented in multi-chamber cardiac stimulation device such as the stimulation device 100 depicted in FIG. 1.

Certain cardiac pacemakers and defibrillators incorporate a pacing lead in the right ventricle and may also include a second lead in the right atrium. High-burden right ventricle apical pacing may contribute to the development of pacing-induced cardiomyopathy and symptoms associated with heart failure (HF). Several pathophysiologic mechanisms have been implicated in the development of pacing-induced HF, each of which likely stems from non-physiological electrical and mechanical activation patterns produced by right ventricle pacing. HBP has been shown to restore physiological activation patterns by utilizing a patient's intrinsic conduction system, even in the presence of bundle branch block. HBP has also been shown to provide significant QRS narrowing, with improved ejection fraction.

Another possible clinical application of HBP is cardiac resynchronization therapy (CRT). Conventional CRT systems include pacing from both a right ventricular and a left ventricular lead, and have been shown to be most effective for patients exhibiting a wide QRS complex and left bundle branch block. HBP has also been shown to be effective at narrowing the QRS complex in patients with left bundle branch block, likely due to restoration of conduction through the Purkinje fibers, which include right and left bundle fibers that are longitudinally dissociated. Therefore, what is thought of as left bundle branch block, can be a result of a proximal blockage within the His bundle that eventually branches to the left bundle. By pacing the His bundle distal to the blockage, a normalized QRS complex can be achieved in some patients. Theoretically, this pacing mode may provide even better results than known CRT treatments, as activation propagates rapidly through natural conduction pathways.

Depending on electrode position, pacing output, patient physiology, and other factors, pacing impulses delivered to the His bundle may result in capture of different cardiac tissue. As used herein, the term "capture" refers to when a pacing impulse has sufficient energy to depolarize cardiac tissue, thereby causing the depolarized cardiac tissue to contract. In the context of HBP, pacing of the His bundle will generally result in one of four capture scenarios: non-selective (NS) His bundle capture, selective (S) His bundle capture, myocardium-only (Myo) capture, or loss of capture (LOC) (aka non-capture). Non-selective capture refers to when a pacing impulse results in capture of both the His bundle and the local myocardium surrounding the His bundle. Because of the simultaneous depolarization of the His bundle and myocardium, non-selective His bundle capture generally results in a combined or condensed electrical response as compared to normal heart activity in which the His bundle and myocardium are depolarized sequentially. Accordingly, non-selective His bundle capture may be characterized by a shortened delay between application of the pacing impulse and ventricular depolarization (e.g., on the order of 20 ms) because the myocardial depolarization propagates immediately without exclusively traveling through the His-Purkinje system. Nevertheless, because the His bundle is stimulated and captured, the QRS duration is similar to the native QRS duration but may be slightly longer due to the myocardial excitation (e.g., 70-120 ms). In contrast, selective His bundle capture refers to exclusive capture of the His bundle without depolarization of the surrounding myocardial tissue. With selective His bundle capture, the stimulus to ventricular depolarization interval is virtually the same as the native delay between His bundle activation and subsequent ventricular depolarization and the QRS duration is essentially identical to the native QRS duration. In myocardium-only capture, the tissue surrounding the His bundle is captured without capturing the His bundle itself, resulting in slow or delayed signal conduction and activation. Finally, loss of capture generally refers to circumstances in which the applied stimulus is insufficient or otherwise unable to elicit a response. In such cases, backup pacing may be applied. For patients with branch bundle block or similar conduction disorders, the foregoing capture types may be further characterized by whether they result in correction of the conduction disorder. For example, a pacing impulse may result in any of non-selective His bundle capture with correction, non-selective His bundle capture without correction, selective His bundle capture with correction, or selective His bundle capture without correction.

While both selective and non-selective His bundle capture may be used to improve cardiac function, selective His bundle capture is generally preferred as the corresponding response more closely approximates natural heart function. However, due to the complexity and dynamic nature of certain cardiomyopathies and cardiac anatomies, selective His bundle capture may not be possible or, if possible at one time, may no longer be possible as a patient's condition changes over time. Moreover, a patient's condition may also progress such that His bundle capture (whether selective or non-selective) may become unavailable and, as a result, direct ventricular pacing may be required.

In light of the foregoing, methods and apparatuses directed to optimizing HBP have been developed, examples of which are disclosed in commonly assigned U.S. Provisional Patent Application No. 62/948,047, titled AUTOMATIC PACING IMPULSE CALIBRATION USING PACING RESPONSE TRANSITIONS filed Dec. 13, 2019, which is incorporated herein by reference. More specifically, the aforementioned patent application describes stimulation devices capable of HBP and processes that may be implemented by such stimulation devices to initialize device settings. To do so, stimulation devices or a programming unit in communication with the stimulation device executes a capture threshold test in which response data is collected for a range of pacing impulse energies (e.g., a range of pacing impulse voltages, pacing impulse pulse widths, or combinations thereof). In certain implementations, the response data may include unipolar, bipolar, or both unipolar and bipolar responses (e.g., IEGMs) recorded and stored by the stimulation device or programming unit. Transitions between capture types are then identified by analyzing changes in response characteristics for the various pacing impulse energy settings that were tested. Based on the number of observed transitions, the nature of the changes indicating the transitions (e.g., how the particular response characteristics change), an initial capture type, and/or other similar factors, the capture pacing impulse energies may then be assigned a capture type. The stimulation device or programming unit may then identify capture thresholds based on the pacing impulse energies at which transitions between different capture types occur and calibrate or adjust stimulation device settings to the best available pacing impulse energy (e.g., the lowest energy (the lowest voltage, pulse width, or combination thereof) for which HBP capture is achieved) according to the assigned capture types and/or identified capture thresholds. By relying on response data obtained from the patient, the settings of the stimulation device are specifically tailored to the individual patient and, as a result, improve both pacing reliability and overall life and function of the stimulation device.

As noted above in the Background, the close proximity of the His bundle to the basal-septal atrial myocardium, AV node, and basal-septal ventricular myocardium presents unique challenges to medical personnel that perform implants, especially those new to His implants. AV node capture or simultaneous His and atrial capture may not be immediately apparent during an implant procedure without performing additional testing. In cases with successful His capture, the multi-signal components (one or more of atrial, His, and ventricular signal) in a His IEGM could also disrupt implantable device logic and impair its normal functionality. For example, a large atrial signal component, if present on the His bipolar or unipolar IEGM, can cause atrial oversensing and have undesirable consequences. For example, where a device algorithm for automated measurement of His capture type and threshold relies on a bipolar and unipolar evoked response, such an algorithm may provide inaccurate results if atrial oversensing occurs. Additionally, a large atrial signal component or unintended atrial and AV node capture may cause unreliable sensing of the HBP evoked response, thus rendering the algorithm inaccurate. Certain embodiments of the present disclosure are related to atrial oversensing testing, atrial capture testing, and AV node testing. As will be appreciated by the description below, the results of such testing can be used in various different manners to improve the use of HBP and/or to improve an implant procedure where the desire it to implant a lead and/or electrode in or proximate to the His bundle.

Before providing additional details of the embodiments of the preset disclosure, FIGS. 1-4 are first used to generally describe the components and functionality of example stimulation devices that may be used to implement aspects of the present disclosure. It should be appreciated that FIGS. 1-4 should be understood to be representative only and are therefore non-limiting. Rather, the methods and techniques described herein may be implemented using any suitable stimulation system/device capable of pacing the His bundle and obtaining and analyzing corresponding response data to such pacing activities. For example and unless otherwise specifically noted, stimulation devices in accordance with the present disclosure may include any number of leads configured to provide stimulation and/or pacing as described herein and may include either unipolar or bipolar leads. Moreover, it should further be understood that the methods disclosed herein may also be performed, at least in part, by an external testing or programming unit capable of receiving and transmitting data from an implantable stimulation device. Such data may include, without limitation, response data measured by the stimulation device and transmitted to the external unit and configuration data transmitted from the external unit to the stimulation device to configure the stimulation device. Further, it should be noted that instead of using a His bundle lead to deliver HBP pulses, and to sense His IEGMs, it would also be possible to use a leadless cardiac pacemaker (LCP) that is implanted at least partially within or adjacent to the His bundle to deliver HBP pulse, and/or sense His IEGMs, and more generally, to perform or otherwise implement the embodiments described herein.

Referring to FIG. 1, a stimulation device 110 is shown in electrical communication with a patient's heart 112 by way of four leads, 120, 121, 124, and 130 and is therefore suitable for delivering multi-chamber stimulation and shock therapy. To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage or atrial septum.

To sense left atrial and ventricular cardiac signals and to provide left chamber pacing therapy, the stimulation device 110 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle.

Accordingly, an exemplary coronary sinus lead 124 is designed to receive atrial and ventricular cardiac signals and to deliver left ventricular pacing therapy using at least a left ventricular tip electrode 126, left atrial pacing therapy using at least a left atrial ring electrode 127, and shocking therapy using at least a left atrial coil electrode 128. In another embodiment, an additional electrode for providing left ventricular defibrillation shocking therapy may be included in the portion of the lead overlying the left ventricle, adjacent to the ring electrode 125.

The stimulation device 110 illustrated in FIG. 1 is generally configured as an implantable cardioverter-defibrillator (ICD) and generally includes functionality for pacing, sensing, and providing defibrillation to a patient heart. It should be appreciated however, that the ICD illustrated in FIG. 1 is just one example stimulation device that may implement aspects of the present disclosure. Other configurations and types of implantable stimulation devices incorporating aspects of the present disclosure are also contemplated. For example and without limitation, in at least one implementation, the stimulation device 110 of FIG. 1 may instead be configured as a pacemaker without defibrillation functionality and, in particular, a pacemaker configured to provide cardiac resynchronization therapy (CRT). In such implementations, some or all of the defibrillation coils illustrated on the various leads of FIG. 1 and their associated circuitry within the stimulation device 110 may be omitted. It should also be appreciated that the specific configuration of leads and placement of leads illustrated in FIG. 1 is intended merely as an example and other configurations are possible. For example, in one specific implementation, the coronary sinus lead 124 may instead be replaced with a left ventricle lead that extends and is implanted within the left ventricle for pacing and/or sensing of the left ventricle. More generally, implementations of the present disclosure are generally applicable to any suitable stimulation devices currently known or later developed that provide His bundle pacing.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular coil electrode 136, and a superior vena cava (SVC) coil electrode 138. Typically, the right ventricular lead 130 is transvenously inserted into the heart 112 so as to place the right ventricular tip electrode 132 in the right ventricular apex so that the right ventricular coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle.

The stimulation device 110 is further connected to a His bundle lead 121 having a His tip electrode 116, such as a helical active fixation device, and a His ring electrode 119 located proximal from the His tip electrode 116. In certain implementations, the His ring electrode 119 is located approximately 10 mm proximal the His tip electrode 116. The His bundle lead 121 may be transvenously inserted into the heart 112 so that the His tip electrode 116 is positioned in the tissue of the His bundle. Accordingly, the His bundle lead 121 is capable of receiving depolarization signals propagated in the His bundle and exiting the Purkinje fibers to the myocardium or delivering stimulation to the His bundle, creating a depolarization that can be propagated through the lower conductive pathways of the right and left ventricles (i.e., the right and left bundle branches and Purkinje fibers). The His bundle lead 121 will be described in greater detail below in conjunction with FIG. 4.

Figure 2:
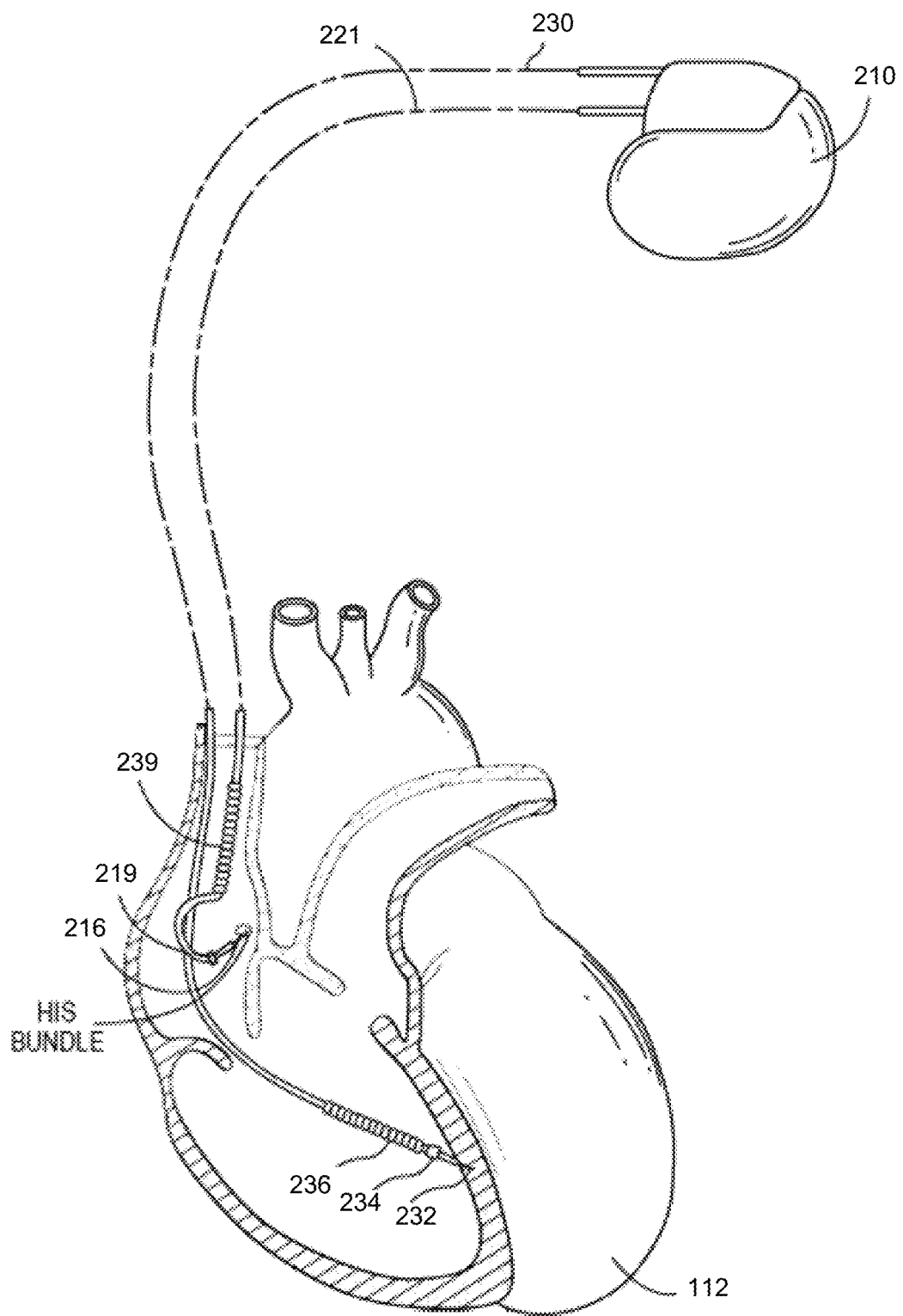
FIG. 2 is a simplified, partly cutaway view illustrating an alternative design of an implantable stimulation device, shown implanted into the right chambers of the patient's heart for delivering dual-chamber stimulation and shock therapy.

An alternative embodiment of the present disclosure is shown in FIG. 2 in which a dual chamber stimulation device 210 is in communication with one atrium, one ventricle, and the His bundle. Though not explicitly illustrated in FIG. 2, a right atrial lead 120 (shown in FIG. 1) can be optionally included. In such implementations, the stimulation device 210 maintains communication with the right atrium of the heart 112 via a right atrial lead 220 having at least an atrial tip electrode 222 and an atrial ring electrode 223 (which may be implanted in the patient's right atrial appendage as described earlier in connection with FIG. 1), and an SVC coil electrode 239

A His bundle lead 221, having a His tip electrode 216 and a His ring electrode 219, is positioned such that the His tip electrode 216 is proximate the His bundle tissue. The stimulation device 210 is shown in FIG. 2 in electrical communication with the patient's heart 112 by way of a right ventricular lead 230 including a right ventricular tip electrode 232, a right ventricular ring electrode 234, and a right ventricular coil electrode 236.

Figure 3:
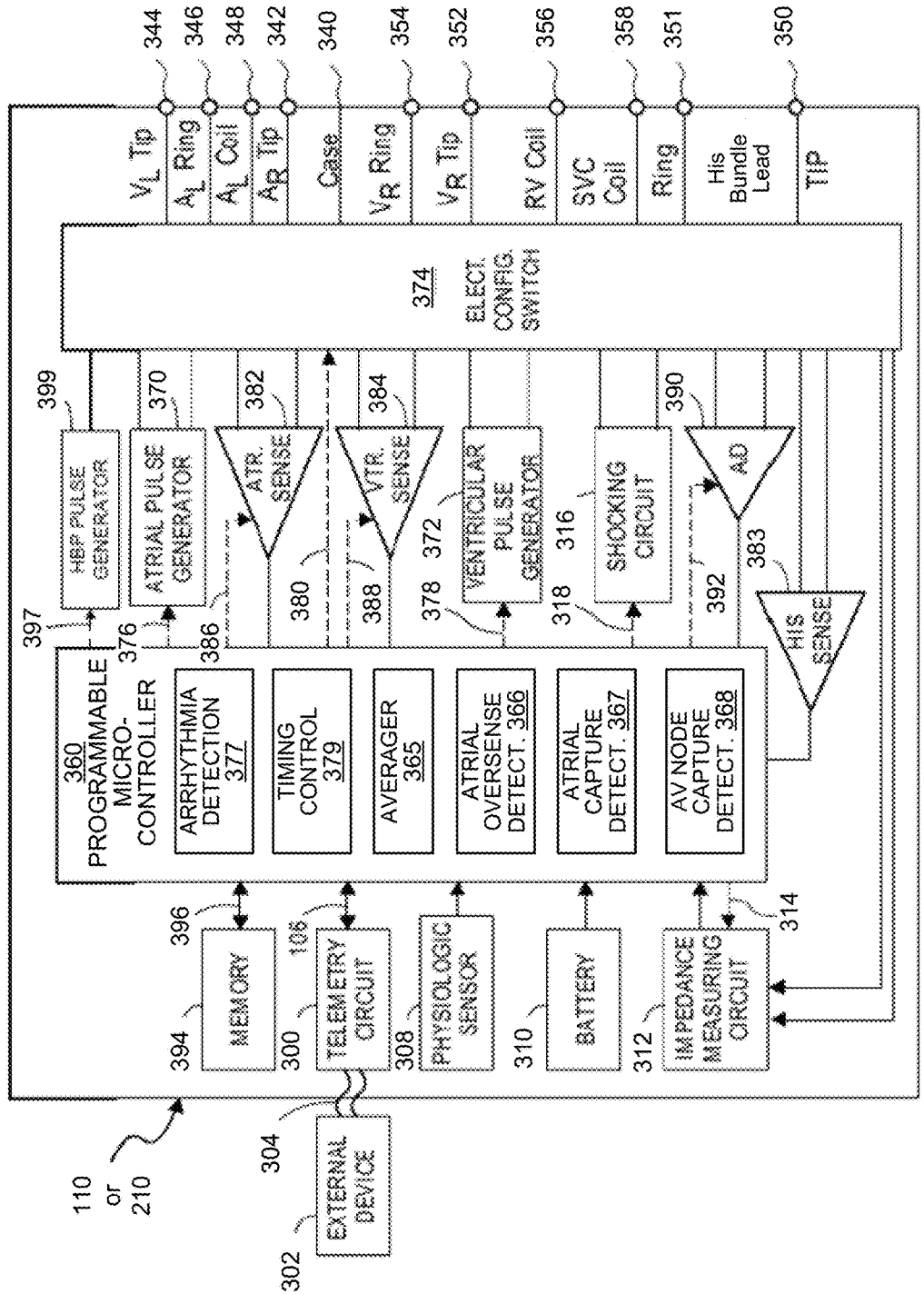
FIG. 3 is a functional block diagram of the multi-chamber implantable stimulation device of FIG. 1 or 2, illustrating the basic elements that provide pacing stimulation, cardioversion, and defibrillation in four (or less) chambers of the heart.

Referring now to FIG. 3, there is illustrated a simplified block diagram of the multi-chamber implantable stimulation device 110 of FIG. 1 (or 210 of FIG. 2), which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 340 for the stimulation device 110 or 210, shown schematically in FIG. 3, is often referred to as the "can", "case" or "case electrode" and may be programmably selected to act as the return electrode for all "unipolar" modes. The housing 340 may further be used as a return electrode alone or in combination with one or more of the coil electrodes 128, 136, and 138 (shown in FIG. 1), or 236 and 239 (shown in FIG. 2) for shocking purposes. The housing 340 further includes a connector (not shown) having a plurality of terminals 342, 344, 346, 348, 350-52, 354, 356, and 358 (shown schematically and, for convenience, next to the names of the electrodes to which they are connected). As such, to achieve right atrial sensing and pacing, the connector includes at least a right atrial tip terminal (AR TIP) 342 adapted for connection to the atrial tip electrode 222 (shown in FIG. 2).

To achieve left chamber sensing, pacing, and defibrillation (in applications in which the stimulation device 110 or 210 is an ICD), the connector includes at least a left ventricular tip terminal (VL TIP) 344, a left atrial ring terminal (AL RING) 346, and a left atrial shocking terminal (AL COIL) 348, which are adapted for connection to the left ventricular tip electrode 126, the left atrial ring electrode 127, and the left atrial coil electrode 128, respectively (each shown in FIG. 1).

To support right chamber sensing, pacing and shocking, the connector further includes a right ventricular tip terminal (VR TIP) 352, a right ventricular ring terminal (VR RING) 354, a right ventricular shocking terminal (RV COIL) 356, and an SVC shocking terminal (SVC COIL) 358, which are adapted for connection to the right ventricular tip electrode 132, right ventricular ring electrode 134, the right ventricular coil electrode 136, and the SVC coil electrode 138, respectively (each shown in FIG. 1).

To achieve His bundle sensing, or sensing and stimulation, the connector further includes a His bundle lead tip terminal 350 and a His bundle lead ring terminal 351 which are adapted for connection to the His tip electrode 116 and the His ring electrode 119, respectively (each shown in FIG. 1).

At the core of the stimulation device 110 or 210 is a programmable microcontroller 360 which controls the various modes of stimulation therapy. The microcontroller 360 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the present disclosure. Rather, any suitable microcontroller 360 may be used that carries out the functions described herein.

As shown in FIG. 3, an atrial pulse generator 370, a ventricular pulse generator 372, and a HBP pulse generator 399 generate pacing stimulation pulses for delivery by the right atrial lead 120, the right ventricular lead 130, the coronary sinus lead 124, and/or the His bundle lead 121 (or 221) via an electrode configuration switch 374. As previously noted, in certain applications, the coronary sinus lead 124 may instead be substituted with a left ventricle lead. It is understood that in order to provide stimulation therapy in each of the chambers of the heart and/or to specific structures of the heart (e.g., the His bundle), the atrial, ventricular, and HBP pulse generators 370, 372, 399 may include dedicated, independent pulse generators, multiplexed pulse generators, or shared pulse generators. The pulse generators 370, 372, 399 are controlled by the microcontroller 360 via appropriate control signals 376, 378, 397, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 360 further includes timing control circuitry 379 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art.

According to one embodiment of the present disclosure, timing control circuitry 379 also controls the onset and duration of a His signal sensing window during which a depolarization signal conducted through the AV node to the His bundle can be detected. Timing control circuitry 379 also controls a timing delay provided after a detected His signal detection, prior to the delivery of a right and/or left ventricular stimulation pulse.

The switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, cross-chamber, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324 (or left ventricle lead), and the right ventricular lead 330, through the switch 374 for detecting the presence of cardiac activity in each of the four chambers of the heart. Accordingly, the atrial (ATR. SENSE) and ventricular (VTR. SENSE) sensing circuits 382, 384 may include dedicated sense amplifiers, multiplexed amplifiers, or shared amplifiers. The switch 374 determines the "sensing polarity" of the cardiac signal by selectively closing the appropriate switches, as is also known in the art. In this way, the clinician may program the sensing polarity independent of the stimulation polarity.

According to one implementation of the present disclosure, a His sensing circuit 383 is selectively coupled to the His bundle lead 121 (shown in FIG. 1) or 221 (shown in FIG. 2) for detecting the presence of a conducted depolarization arising in the atria and conducted through the His bundle via the AV node. As used herein, each of the atrial sensing circuit 382, the ventricular sensing circuit 384, and the His sensing circuit 383, includes a discriminator, which is a circuit that senses and can indicate or discriminate the origin of a cardiac signal in each of the cardiac chambers.

As illustrated in FIG. 3, the His sensing circuit 383 is shown as a dedicated circuit within the stimulation device 110 or 210. However, it should be appreciated that in certain implementations, His-related functionality may instead be provided by repurposing other pacing and sensing channels and circuitry of the stimulation device 110 or 210. For example, the stimulation device 110 or 210 may be reprogrammed such that a pacing channel, a sensing channel, and associated circuitry initially programmed for use in sensing and pacing one of the atria or ventricles may instead be reconfigured to pace and sense the His bundle.

Each sensing circuit 382-384 preferably employs one or more low power, precision amplifiers with programmable gain and/or automatic gain control, bandpass filtering, and a threshold detection circuit to selectively sense the cardiac signal of interest. The automatic gain control enables the device 110 or 210 to deal effectively with the difficult problem of sensing the low amplitude signal characteristics of atrial or ventricular fibrillation.

The outputs of the sensing circuits 382-384 are connected to the microcontroller 360 which, in turn, is able to trigger or inhibit the atrial and ventricular pulse generators 370, 372, respectively, in a demand fashion in response to the absence or presence of cardiac activity in the appropriate chambers of the heart.

The atrial and ventricular sensing circuits 382, 384, in turn, receive control signals over signal lines 386, 388, from the microcontroller 360 for purposes of controlling the gain, threshold, polarization charge removal circuitry (not shown), and the timing of any blocking circuitry (not shown) coupled to the inputs of the sensing circuits 382, 384.

Similarly, the output of the His sensing circuit 383 is connected to the microcontroller 360 which, in turn, is able to trigger or inhibit the HBP pulse generator 399 in a demand fashion in response to the absence or presence of cardiac activity associated with the His bundle. The His sensing circuit 383 may also receive control signals from the microcontroller 360 for purposes of controlling gain, threshold, polarization charge removal circuitry, and the timing of any blocking circuitry coupled to the inputs of the His sensing circuit 383.

As described below in further detail certain aspects of controlling or configuring the HBP pulse generator 399 may also be based on measurements related to activity of other structures/chambers of the heart. So, for example and without limitation, the HBP pulse generator 399 may also be triggered, inhibited, calibrated, or configured based on outputs from the atrial and ventricular sensing circuits 382-384 or any other similar sensing circuit adapted to measure electrical activity of the heart.

For arrhythmia detection, the stimulation device 110 or 210 includes an arrhythmia detector 377 that utilizes the atrial and ventricular sensing circuits 382, 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 360 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 390 represented by an A/D converter. The data acquisition system 390 is configured to acquire intracardiac electrogram signals, convert the raw analog data into a digital signal, and store the digital signals for later processing and/or telemetric transmission to an external device 302. The data acquisition system 390 is coupled to the right atrial lead 120, the His bundle lead 121 (or 221), the coronary sinus lead 124, and the right ventricular lead 130 (or 230) through the switch 374 to sample cardiac signals across any pair of desired electrodes.

In one embodiment, the data acquisition system 390 is coupled to microcontroller 360, or to other detection circuitry, for detecting a desired feature of the His bundle signal. In one embodiment, an averager 365 is used to determine a sliding average of the His bundle signal during a His signal sensing window using known or available signal averaging techniques.

Advantageously, the data acquisition system 390 may be coupled to the microcontroller 360, or other detection circuitry, for detecting an evoked response from the heart 112 in response to an applied stimulus, thereby aiding in the detection of capture. The microcontroller 360 detects a depolarization signal during a window following a stimulation pulse, the presence of which indicates that capture has occurred. The microcontroller 360 enables capture detection by triggering the ventricular pulse generator 372 to generate a stimulation pulse, starting a capture detection window using the timing control circuitry 379 within the microcontroller 360, and enabling the data acquisition system 390 via control signal 392 to sample the cardiac signal that falls in the capture detection window and, based on the amplitude, determines if capture has occurred.

Capture detection may occur on a beat-by-beat basis or on a sampled basis. Preferably, a capture threshold search is performed at least once a day during at least the acute phase (e.g., the first 30 days following device implant) and less frequently thereafter. A capture threshold search would begin at a desired starting point (either a high energy level or the level at which capture is currently occurring) and decrease the energy level until capture is lost. The minimum energy at which capture is consistently obtained is known as the capture threshold. Thereafter, a safety margin can be automatically or programmably added to the capture threshold.

Capture detection and threshold testing may also be performed for purposes of His bundle pacing. Processes for performing capture threshold testing for His bundle pacing and configuring the stimulation device 110 or 210 based on the results of such testing are described in more detail below.

The microcontroller 360 is further coupled to a memory 394 by a suitable data/address bus 396, wherein the programmable operating parameters used by the microcontroller 360 are stored and modified, as required, in order to customize the operation of the stimulation device 310 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy.

Advantageously, the operating parameters of the implantable device 110 may be non-invasively programmed into the memory 394 through a telemetry circuit 300 in telemetric communication with the external device 302, such as a programmer, transtelephonic transceiver, or a diagnostic system analyzer. The telemetry circuit 300 is activated by the microcontroller 360 by a control signal 306. The telemetry circuit 300 advantageously allows intracardiac electrograms and status information relating to the operation of the device 110 or 210 (as contained in the microcontroller 360 or memory 394) to be sent to the external device 302 through an established communication link 304.

In certain implementations, the stimulation device 110 or 210 may further include a physiologic sensor 308, commonly referred to as a "rate-responsive" sensor to adjust pacing stimulation rate according to the exercise state of the patient. However, the physiological sensor 308 may further be used to detect changes in cardiac output, changes in the physiological condition of the heart, or diurnal changes in activity (e.g., detecting sleep and wake states). Accordingly, the microcontroller 360 responds by adjusting the various pacing parameters (such as rate, stimulation delays, etc.) at which the atrial and ventricular pulse generators 370, 372 generate stimulation pulses.

A common type of rate responsive sensor is an activity sensor, such as an accelerometer or a piezoelectric crystal, which is mounted within the housing 340 of the stimulation device 110 or 210. Other types of physiologic sensors are also known, for example, sensors which sense the oxygen content of blood, respiration rate, and/or minute ventilation, pH of blood, ventricular gradient, etc. However, any suitable sensor may be used which is capable of sensing a physiological parameter which corresponds to the exercise state of the patient. The type of sensor used is not critical to the present disclosure and is shown only for completeness.

The stimulation device 110 or 210 additionally includes a battery 310 which provides operating power to all of the circuits shown in FIG. 3. For the stimulation device 110 or 210, which employs shocking therapy, the battery 310 must be capable of operating at low current drains for long periods of time, and then be capable of providing high-current pulses (for capacitor charging) when the patient requires a shock pulse. The battery 310 must also have a predictable discharge characteristic so that elective replacement time can be detected. Accordingly, the device 110 or 210 preferably employs lithium/silver vanadium oxide batteries, as is true for most (if not all) current devices.

The device 110 or 210 is shown in FIG. 3 as having an impedance measuring circuit 312 which is enabled by the microcontroller 360 via a control signal 314. The known uses for an impedance measuring circuit 312 include, but are not limited to, lead impedance surveillance during the acute and chronic phases for detecting proper lead positioning or dislodgement; detecting operable electrodes and conductors; and automatically switching to an operable pair if dislodgement or electrical disruption occurs; measuring respiration or minute ventilation; measuring thoracic impedance for determining shock thresholds; detecting when the device has been implanted; measuring stroke volume; and detecting the opening of heart valves, etc. The impedance measuring circuit 312 is advantageously coupled to the switch 374 so that any desired electrode may be used.

In certain implementations of the present disclosure, the device 110 or 210 may be configured to perform beat-by-beat impedance monitoring in conjunction with measuring and monitoring other electrical activity (e.g., generating IEGMs) for each beat. In such applications, the measured impedance may generally provide further information regarding the occurrence and potential cause of changes in the electrical activity, including, without limitation, changes in His bundle capture type or capture quality.

Figure 4:
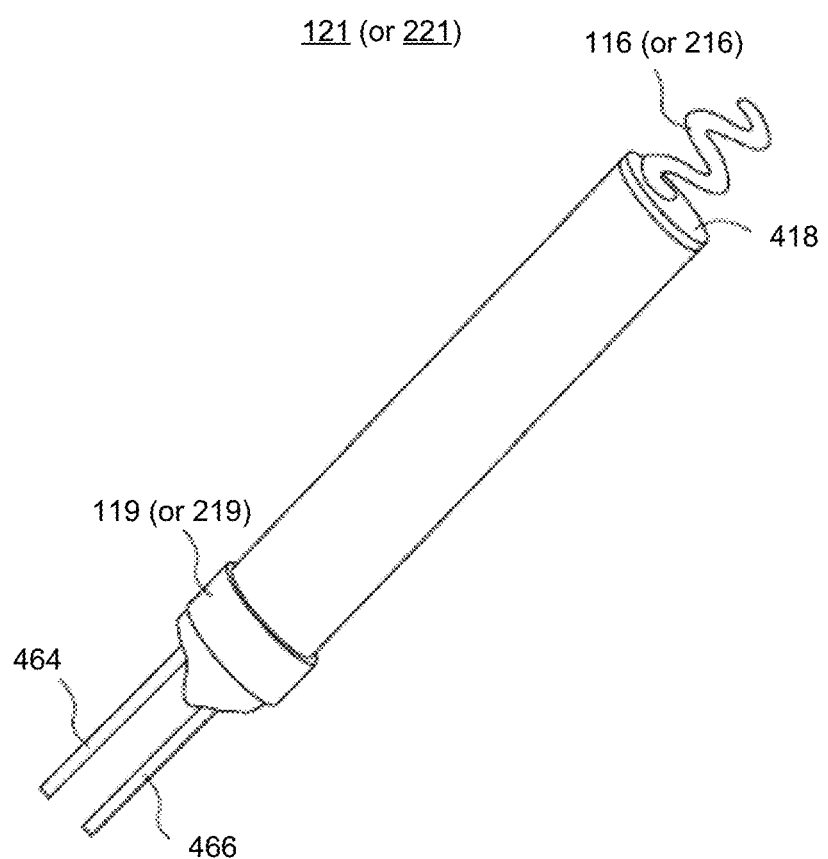
FIG. 4 is a partly fragmentary illustration of the distal end of the His bundle lead for use with the stimulation device of FIG. 3, depicting a tip electrode with an active fixation device and a non-traumatic conductive surface, and a ring electrode.

According to one implementation of the present disclosure, the His tip electrode 116 (or 216) and His ring electrode 119 (or 219) may be selectively coupled via switch 374 to the impedance measuring circuit 312 for performing a tissue impedance measurement. The tissue impedance measurement may be made to determine the location of the His bundle as the His tip electrode 116 (or 216) or mapping collar 418 as shown in FIG. 4, or sensing electrodes advanced along the endocardial surface of the right atrium. In other implementations of the present disclosure, alternative approaches for mapping the intrinsic conduction signals of the His bundle and associated tissue may be used. For example and without limitation, in at least one implementation an electrophysiology (EP) catheter may be used to identify a location for the His tip electrode 116 (or 216).

In the case where the stimulation device 110 or 210 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 360 further controls a shocking circuit 316 by way of a control signal 318. The shocking circuit 316 generates shocking pulses of low (for example, up to 0.5 joules), moderate (for example, 0.5-10 joules), or high energy (for example, 11-40 joules), as controlled by the microcontroller 60. Such shocking pulses are applied to the patient's heart 112 through at least two shocking electrodes, and as shown in this embodiment, selected from the left atrial coil electrode 128, the right ventricular coil electrode 136 (or 236), and the SVC coil electrode 138. As noted above, the housing 340 may act as an active electrode in combination with the right ventricular electrode 136, or as part of a split electrical vector using the SVC coil electrode 138 or the left atrial coil electrode 128 (i.e., using the right ventricular electrode 136 as a common electrode). As previously noted, the implementation illustrated in FIG. 1 is provided as an example and other configurations are possible. For example, in other implementations, the high voltage coils for both RV coil and SVC coil may be disposed on the right ventricle lead as opposed to the RA lead.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

A more detailed illustration of the His bundle lead 121 (or 221) is shown in FIG. 4. At the distal end of the lead 121 (or 221) is the His bundle tip electrode 116 (or 216). The His bundle tip electrode 116 (or 216) is, or includes, an active fixation device, such as a helical, "screw-in," device that allows stable fixation of the electrode in the His bundle tissue.

The distal end of the His bundle lead 121 (or 221) is further provided with a non-traumatic conductive surface (also referred to herein interchangeably as a mapping collar) 418. The non-traumatic conductive surface 418 is advantageously used to make electrical measurements that indicate the location of the His bundle without having to anchor the His bundle tip electrode 116 (or 216) into the endocardial tissue. The non-traumatic conductive surface 418 and the His bundle tip electrode 116 are electrically coupled within the lead body of the His bundle lead 121 (or 221) and together form one conductive element for the purposes of sensing, stimulation, and impedance measurements.

The His bundle lead 121 (or 221) is also provided with a His ring electrode 119 (or 216). The His ring electrode 119 (or 219) is preferably spaced between approximately 2 mm and 30 mm, but preferably 10 mm, from the His tip electrode 116 (or 216). The His ring electrode 119 (or 219) may function as the return electrode during bipolar sensing, stimulation or impedance measurement operations.

The His tip electrode 116 (or 216) and the His ring electrode 119 (or 219) are each connected to flexible conductors 464, 466, respectively, which may run the entire length of the His bundle lead 121 (or 221). The flexible conductor 464 is connected to the His tip electrode 116 (or 216) and is electrically insulated from the flexible conductor 466 by a layer of insulation. The conductor 466 is connected to the His ring electrode 119 (or 219). The flexible conductors 464, 466 serve to electrically couple the His ring electrode 119 (or 219) and the His tip electrode 116 (or 216) to the His ring electrode terminal 351 and the His tip electrode terminal 350, respectively. One embodiment of the His bundle lead 121 (or 221) is available from St. Jude Medical CRMD as lead model No. 2088T.

In accordance with certain embodiments, an excitation current is applied through the His tip electrode 116 (or 216). A voltage signal can then be measured between the His tip electrode 116 (or 216) (or the non-traumatic conductive surface 418) and the His ring electrode 119 (or 219) in a bipolar fashion. The voltage signal is related to the supplied current and the tissue impedance associated with the tissue in contact with the His tip electrode 116 (or 216). Thus, the measured voltage signal is processed by the impedance measuring circuit 312 to determine the impedance of the tissue in contact with His tip electrode 116 (or 216). The impedance equals the voltage divided by the current.

The His tip electrode 116 (or 216) may then be secured in the His bundle thereby anchoring the His tip electrode 116 (or 216) in contact with the His bundle tissue. The electrogram signal arising from the His bundle can then be received by the His sensing circuit 383. A bypass filter (not shown) that allows signals ranging from 30-200 Hz to be received may be used to block the high frequency alternating current excitation signal produced by an oscillator.

It should be appreciated that the His bundle lead and associated components illustrated in FIG. 4 are provided merely as examples and should not be viewed as limiting this disclosure to requiring any particular type of lead. Rather, aspects of the present current disclosure may be implemented using any suitable His bundle lead capable of being implanted at or near the His bundle and providing pacing impulses to the His bundle. Further, it should be noted that instead of using a His bundle lead to deliver HBP pulses, and to sense His IEGMs, it would also be possible to use a leadless cardiac pacemaker (LCP) that is implanted at least partially within or adjacent to the His bundle to deliver HBP pulse, and/or sense His IEGMs.

Referring again to FIG. 3, the microcontroller 360 is also shown as including an atrial oversense detector 366, an atrial capture detector 367, and an AV node capture detector 368. The atrial oversense detector 366 is configured to perform an atrial oversensing test to determine, inter alia, whether or not atrial oversensing is detected within a His IEGM. Additional details of various such atrial oversensing tests, according to embodiments of the present technology, are described below with reference to FIGS. 5-9. The atrial capture detector 367 is configured to perform an atrial capture test to determine whether atrial capture occurs in response to his bundle pacing (HBP). Additional details of such an atrial capture test are described below with reference to FIGS. 10-11. The AV node capture detector 368 is configured to perform an AV node capture test to determine whether AV node capture occurs in response to HBP. Additional details of such an AV node capture test are described below with reference to FIGS. 11-12. More generally, the detectors 366, 367, and 368, which can also be referred to as modules, can be used to implement various algorithms and/or methods presented below in the discussion of FIGS. 5-13. The aforementioned detectors 366, 367, and 368 may be implemented in hardware as part of the microcontroller 360, or as software/firmware instructions programmed into the device 110 or 112 and executed on the microcontroller 360 during certain modes of operation. More generally, the detectors 366, 367, and 368 can be implemented using one or more processors.

Atrial Oversensing Testing

As noted above, the close proximity of the His bundle to the basal-septal atrial myocardium, AV node, and basal-septal ventricular myocardium presents unique challenges to medical personnel that perform implants, especially those new to His implants. For example, a large atrial signal component, if present on a His bipolar or unipolar IEGM, can cause atrial oversensing and have undesirable consequences. For example, where a device algorithm for automated measurement of His capture type and threshold relies on a bipolar and unipolar evoked response, such an algorithm may provide inaccurate results if atrial oversensing occurs. Certain embodiments of the present disclosure, which are related to atrial oversensing testing, can be used to determine whether or not atrial oversensing is occurring, and the results of such testing can be used to determine when it is appropriate to perform His bundle capture threshold detection and/or other types of His capture management. Exemplary techniques for performing His bundle capture threshold detection and/or other types of His capture management are described in commonly assigned U.S. Provisional Patent Application No. 62/948,047, titled AUTOMATIC PACING IMPULSE CALIBRATION USING PACING RESPONSE TRANSITIONS filed Dec. 13, 2019, which was incorporated herein by reference above. Since certain HBP capture management techniques rely on robust pacing of the His bundle and accurate sensing of the ventricular evoked response, it is beneficial to only utilizes such HBP capture management techniques in the absence of atrial oversensing (as well as in the absence of atrial capture and AV node capture).

Various embodiments of the present technology, which relate to atrial oversensing testing, are described below with reference to FIGS. 5-9. In accordance with certain embodiment, the atrial oversensing testing described with reference to FIGS. 5-9 can be performed by or under the control of the atrial oversense detector 366, or more generally, using a controller that includes one or more processors and/or a state machine.

Figure 5:
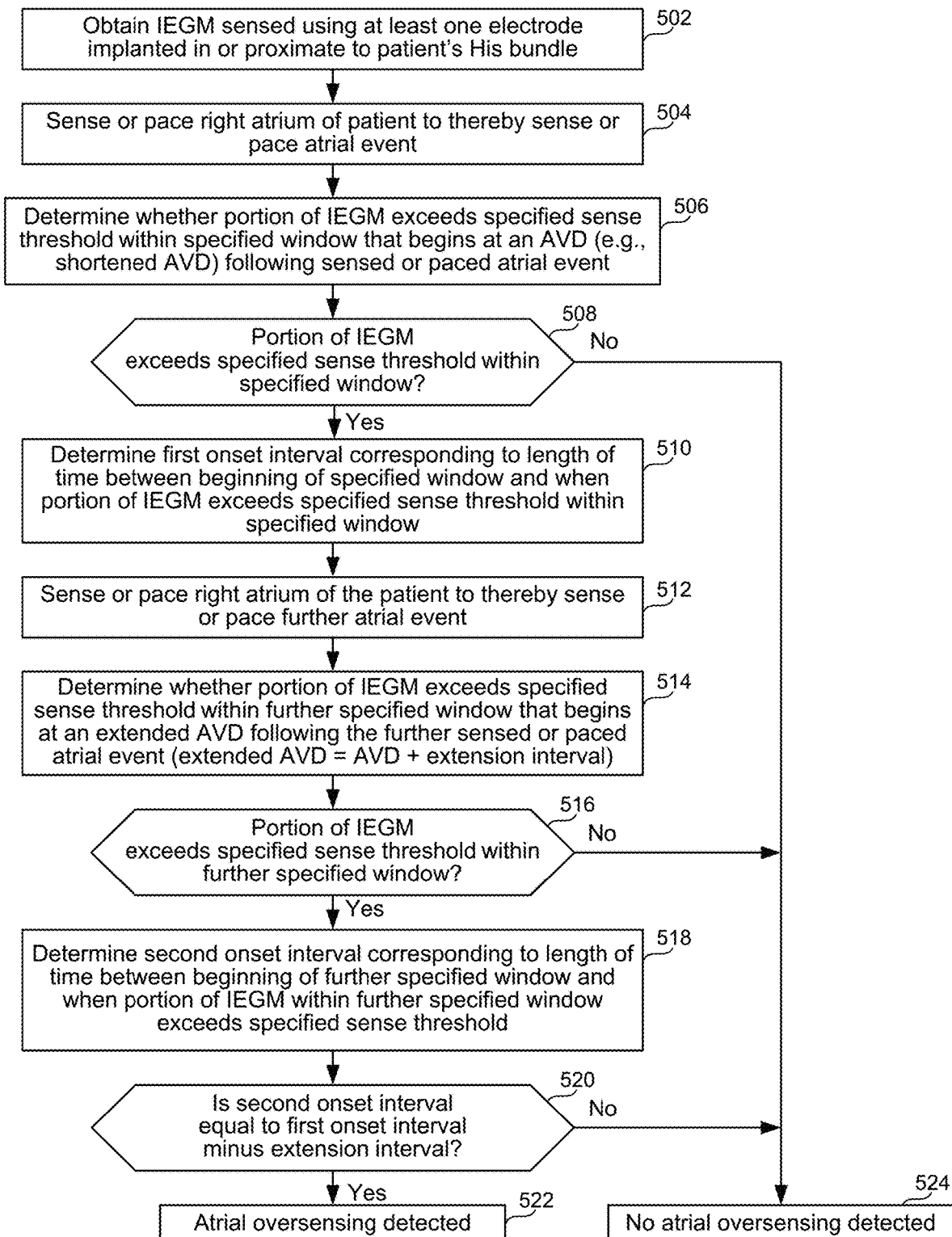
FIG. 5 is a high level flow diagram that is used to describe certain methods for determining whether or not atrial oversensing is detected within a His IEGM.

FIG. 5 is a high level flow diagram that is used to describe certain methods for determining whether or not atrial oversensing is detected within a His IEGM. Such methods can be used with an implantable medical device (e.g., 102 or 202) including one or more electrodes that can be used for sensing and pacing, wherein such a device can make up an entire implantable medical system, or may just be part of (e.g., a subsystem of) an implantable medical system.

Figure 6:
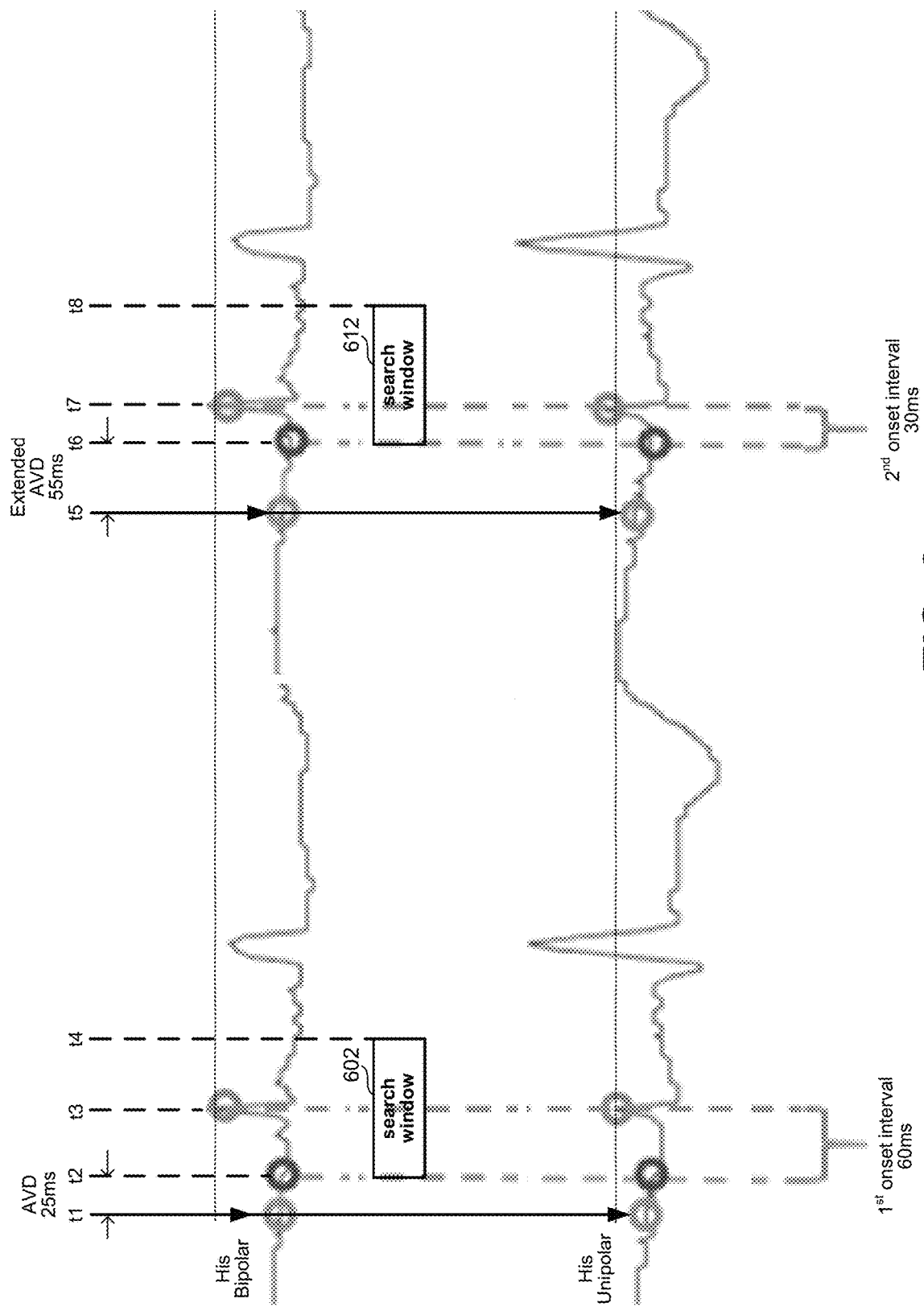
FIG. 6 illustrates example His bipolar and His unipolar IEGMs that are used to explain in more detail how atrial oversensing may be detected using the methods described with reference to the flow diagram of FIG. 5.

Referring to FIG. 5, step 502 involves obtaining an intracardiac electrogram (IEGM) sensed using at least one electrode implanted in or proximate to a patient's His bundle. Since the IEGM obtained at step 502 is sensed using at least one electrode implanted in or proximate to a patient's His bundle, such an IEGM can be referred to more specifically as a His IEGM. The His IEGM obtained at step 502 can be a unipolar His IEGM, wherein a case electrode (e.g., 340) is used as one of the sensing electrodes to obtain the unipolar His IEGM. Alternatively, or additionally, the His IEGM obtained at step 502 can be a bipolar His IEGM, wherein at least two electrodes, not including the case electrode (e.g., 340), are used as the sensing electrodes to obtain the bipolar His IEGM. For specific examples, referring back to FIGS. 1-3, the His tip electrode 116 or 216 (connected His tip electrode terminal 350) and the case electrode 340 can be used to sense a unipolar His IEGM; or the His tip electrode 116 or 216 (connected to the His tip electrode terminal 350) and the His ring electrode 119 or 219 (connected to the His ring electrode terminal 351) can be used to sense a bipolar His IEGM. FIG. 6, discussed below, shows examples of His unipolar and bipolar IEGMs that could be obtained at step 502.

Referring again to FIG. 5, step 504 involves sensing or pacing a patient's right atrium to thereby sense or pace an atrial event. A paced atrial event can also be referred to as an atrial pace (AP), and a sensed intrinsic atrial event can also be referred to as an atrial sense (AS). Step 504 can be performed, e.g., using at least one of the electrodes of the right atrial lead 120, but is not limited thereto.

Step 506 involves determining whether a portion of the His IEGM exceeds a specified sense threshold within a specified window that begins an atrioventricular delay (AVD) following the sensed or paced atrial event. Such a step can be performed by comparing samples of the His IEGM to the specified sense threshold, to thereby determine whether or not at least one of the samples exceeds the specified sense threshold.

Step 508 is a decision block or step, which directs flow to step 510 or to step 524, depending upon the results of step 506. More specifically, at step 508 there is a determination of whether or not there was a determination (at step 506) that a portion of the His IEGM exceeded the specified sense threshold within the specified window. If the answer to the determination at step 508 is No, then flow goes to step 524 and it is concluded that no atrial oversensing was detected. However, if the answer to the determination at step 508 is Yes, then flow goes to step 510. While steps 506 and 508 are shown as two distinct steps in FIG. 5, these steps can alternatively be combined into a single step, as would be appreciated by one skilled in the art.

In accordance with certain embodiments, the specified window, which begins at the AVD following the sensed or paced atrial event (i.e., following the AS or AP) is an evoked response window. In such embodiments, step 506 can involve triggering the evoked response window (at the AVD following the sensed or paced atrial event) by delivering a subthreshold pacing pulse to the patient's His bundle (using at least one electrode that is implanted in or proximate to the patient's His bundle), wherein the subthreshold pacing pulse has energy below a capture threshold associated with the patient's His bundle and the RV myocardium. The subthreshold pacing pulse can, e.g., have an amplitude of 0.25V and a pulse width of 0.05 ms, or can have the minimum amplitude and minimum pulse width setting allowed by the implantable device, but is not limited thereto. Indeed, the subthreshold pacing pulse can have an amplitude of 0V if desired/possible, since its goal is not to cause capture, but rather, is to trigger an evoked response window. For the embodiments summarized with reference to the flow diagram of FIG. 5, the AVD (at the end of which the specified window, e.g., the evoked response window, begins) is preferably short enough such that intrinsic AV conduction does not occur within the specified window (e.g., the evoked response window) within which there is a determination of whether the specified threshold is crossed. For an example, assuming the device performing the method of FIG. 5 is in DDD mode, the AVD used at step 506 can be set to 50 ms following an atrial paced event (aka AP), or the AVD used at step 506 can be set to 25 ms following an atrial sensed event (aka AS). The use of longer or shorter AVD values are also possible, and within the scope of the embodiments described herein. In accordance with certain embodiments, the length of the specified window (e.g., the evoked response window) within which there is a determination of whether the specified threshold is crossed can be 140 ms, or more generally within the range of 120 ms to 160 ms. The use of windows that are longer or shorter than that range are also possible, and within the scope of the embodiments described herein. In accordance with certain embodiments, at the end of the specified window a safety pacing pulse (aka a backup pacing pulse) is delivered to the right ventricle.

In summary, steps 502-508 are performed to determine whether or not atrial oversensing may have potentially occurred. If the answer to the determination at step 508 was No, then as noted above, it is concluded at step 524 that atrial oversensing was not detected. If the answer to the termination at step 508 was Yes, then as noted above, flow goes to step 510. As will be appreciated from the below discussion, steps 510-520 are performed to determine whether or not the His IEGM exceeding the specified sense threshold within the specified window (which resulted in the answer to the determination at step 508 being Yes) was due to atrial oversensing, as opposed to some other factor such as noise, a pacing artifact (if subthreshold pacing has an amplitude greater than 0V), or a premature ventricular contraction (PVC).

Still referring to FIG. 5, step 510 involves determining a first onset interval corresponding to a length of time between a beginning of the specified window and when the portion of the His IEGM exceeded the specified sense threshold within the specified window. Step 512 involves sensing or pacing the right atrium of the patient to thereby sense or pace a further atrial event. Step 514 involves determining whether a portion of the IEGM exceeds the specified sense threshold within a further specified window that begins at an extended AVD following the further sensed or paced atrial event, wherein the extended AVD is equal to the specified AVD (referred to in step 506) plus an extension interval that is less than the first onset interval. For an example, the extension interval can be a fixed value, such as 50 ms. Alternatively, the extension interval can be dynamically determined based on the first onset interval that we determined at step 510.

More specifically, the extension interval can be equal to a specified percentage (e.g., 50%) of the first onset interval, but is not limited thereto. Assuming that the extension interval is equal to 50% of the first interval, then the extended AVD would be equal to the specified AVD (referred to in step 506) plus 50% of the first onset interval (determined at step 510). In accordance with certain embodiments, the further specified window (referred to in step 514) can be a further evoked response window that is triggered by delivering a further subthreshold pacing pulse having energy below a capture threshold associated with the patient's His bundle and the RV myocardium. Step 516 is a decision block or step, which directs flow to step 518 or to step 524, depending upon the results of step 514. More specifically, at step 516 there is a determination of whether or not a portion of the IEGM exceeds the specified sense threshold within the further specified window that begins at the extended AVD following the further sensed or paced atrial event. If the answer to the determination at step 516 is No, then flow goes to step 524 and it is concluded that no atrial oversensing was detected. However, if the answer to the determination at step 516 is Yes, then flow goes to step 518. While steps 514 and 516 are shown as two distinct steps in FIG. 5, these steps can alternatively be combined into a single step, as would be appreciated by one skilled in the art. In accordance with certain embodiments, at the end of the further specified window a safety pacing pulse (aka a backup pacing pulse) is delivered to the right ventricle.

Step 518 involves determining a second onset interval corresponding to a length of time between a beginning of the further specified window and when the portion of the IEGM within the further specified window exceeds the specified sense threshold.

Step 520 involves determining whether the second onset interval is equal to the first onset interval minus the extension interval. Step 520 is a decision block or step, which directs flow to step 522 or to step 524, depending upon the results of steps 518 and 510. More specifically, at step 520 there is a determination of whether or not the second onset interval (determined at step 518) is equal to the first onset interval (determined at step 510) minus the extension interval (referred to in step 514). If the answer to the determination at step 520 is No, then flow goes to step 524 and it is concluded that no atrial oversensing was detected. However, if the answer to the determination at step 520 is Yes, then flow goes to step 522, and it is concluded that atrial oversensing was indeed detected.

Example His bipolar and His unipolar IEGMs, one or both of which can be detected at an instance of step 502, are shown in FIG. 6 and will now be used to explain in more detail how atrial oversensing may be detected using the embodiment summarized with reference to the flow diagram of FIG. 5. Referring to FIG. 6, the time t1 corresponds to a time at which an atrial sensed event (AS) occurred, which AS could be detected at step 504. Still referring to FIG. 6, the time t2 corresponds to a 25 ms AVD following the AS that occurred at the time t1, at which point in time the specified window referred to in step 506 begins. In other words, the 25 ms AVD is an example of the AVD referred to in step 506. The horizontal dotted lines in FIG. 6 are representative of the specified sense threshold (referred to in steps 506 and 508), for which there is a determination of whether the specified threshold is crossed by the His IEGM.

In FIG. 6, the "search window" 602 corresponds to the specified window referred to in step 506, and more specifically, corresponds to the specified window (that begins the AVD following the sensed or paced atrial event) within which there is a determination of whether a portion of the His IEGM exceeds a specified sense threshold. In certain embodiments, the specified window 602 (which can also be referred to as the search window) is an evoke response window that is triggered by delivering a subthreshold pacing pulse, as was discussed above with reference to step 506 in FIG. 5.

In FIG. 6, the time t3 corresponds to a time at which a portion of the His IEGM exceeds the specified sense threshold within the specified window. The interval between the time t2 and the time t3 corresponds to the first onset interval, which is determined at step 510 in FIG. 5. The time t4 is the end of the search window, and thus the search window (aka the specified window) corresponds to the interval between the time t2 and the time t4, in this example.

Still referring to FIG. 6, the time t5 corresponds to a time at which a further atrial sensed event (AS) occurred, which AS could be detected at step 512. The time t6 corresponds to an extended AVD following the AS that occurred at time t5, at which point in time the further specified window 612 referred to in step 514 begins. In other words, the 55 ms AVD is an example of the extended AVD referred to in step 514, wherein the extended AVD in this example is equal to the 25 ms AVD (referred to in step 506) plus 50% of the 60 ms first onset interval determined at step 510, and thus in this example the extended AVD is equal to 55 ms (i.e., 25 ms+0.50*60 ms=55 ms).

In FIG. 6, the time t7 corresponds to a time at which a portion of the His IEGM exceeds the specified sense threshold within the further specified window 612. The interval between the time t6 and the time t7 corresponds to the second onset interval, which is determined at step 518 in FIG. 5. The time t8 is the end of the search window 612, and thus the search window (aka the further specified window) corresponds to the interval between the time t6 and the time t8, in this example. In the example of FIG. 6, the 30 ms second onset interval is indeed equal to the 60 ms first onset interval minus the 30 ms extension interval, and this, the answer to the determination at step 520 in FIG. 5 would be Yes, thereby resulting in atrial oversensing being detected at step 522 in FIG. 5. Due to the intrinsic delay of the AV node, any ventricular signal would occur outside of the search window, as demonstrated in FIG. 6. Only an atrial signal could occur in the search window and result in identical t1 to t3 and t5 to t7 intervals.

In FIG. 6, both a His bipolar IEGM was shown (at the top of the page), and a His unipolar IEGM was shown (at the bottom of the page). However, both types of His IEGMs need not be sensed or used to perform an atrial oversensing test described above with reference to FIG. 5. Nevertheless, if both types of His IEGMs are available for analysis, since both are sensed, the method can be performed for each of the types of His IEGMs, and depending upon the specific implementation, atrial oversensing can be detected when step 522 is reached for at least one of the His IEGMs, or for both of the His IEGMs. The method of FIG. 5 can alternatively be performed for just one of the types of His IEGMs (i.e., unipolar or bipolar).

The medical system, with which an embodiment summarized with reference to FIGS. 5 and 6 is performed, can be configured to selectively perform His capture management. In such a medical system, whenever atrial oversensing is detected, His capture management is not performed, because the His capture management would likely be adversely affected by the atrial oversensing. In other words, in accordance with certain embodiments, a method can include preventing performance of the His capture management in response to detecting atrial oversensing. In such an embodiments, after detecting atrial oversensing, at a later point in time that atrial oversensing is no longer detected, performance of the His capture management is enabled. The aforementioned His capture management can include determining whether His capture occurred in response to delivery of a pacing pulse, determining a capture threshold (e.g., performing His Autocapture), and/or determining a capture type when capture is determined to have occurred.

The embodiments described with reference to FIGS. 5 and 6 are especially useful when an implantable stimulation system/device is in DDD mode, since such a system/device performs pacing at the His lead a specified AVD following an AS or AP if a PVC is not encountered during the specified AVD. Since DDD mode does not provide for a backup pacing pulse at the end of each specified window, delivery of a backup pacing at the end of the search window is preferably programmed into the atrial oversensing test. In accordance with certain embodiments, an implantable stimulation system/device is programmed to deliver a backup pulse to the His bundle at the end of each specified window, which in certain embodiments, are evoked response windows. Each such window (e.g., evoked response window) preferably ends before intrinsic AV conduction is expected. This can be achieved by using sufficiently short AVDs when monitoring for atrial oversensing, and sufficiently short windows (e.g., evoked response windows).

Figure 7A:
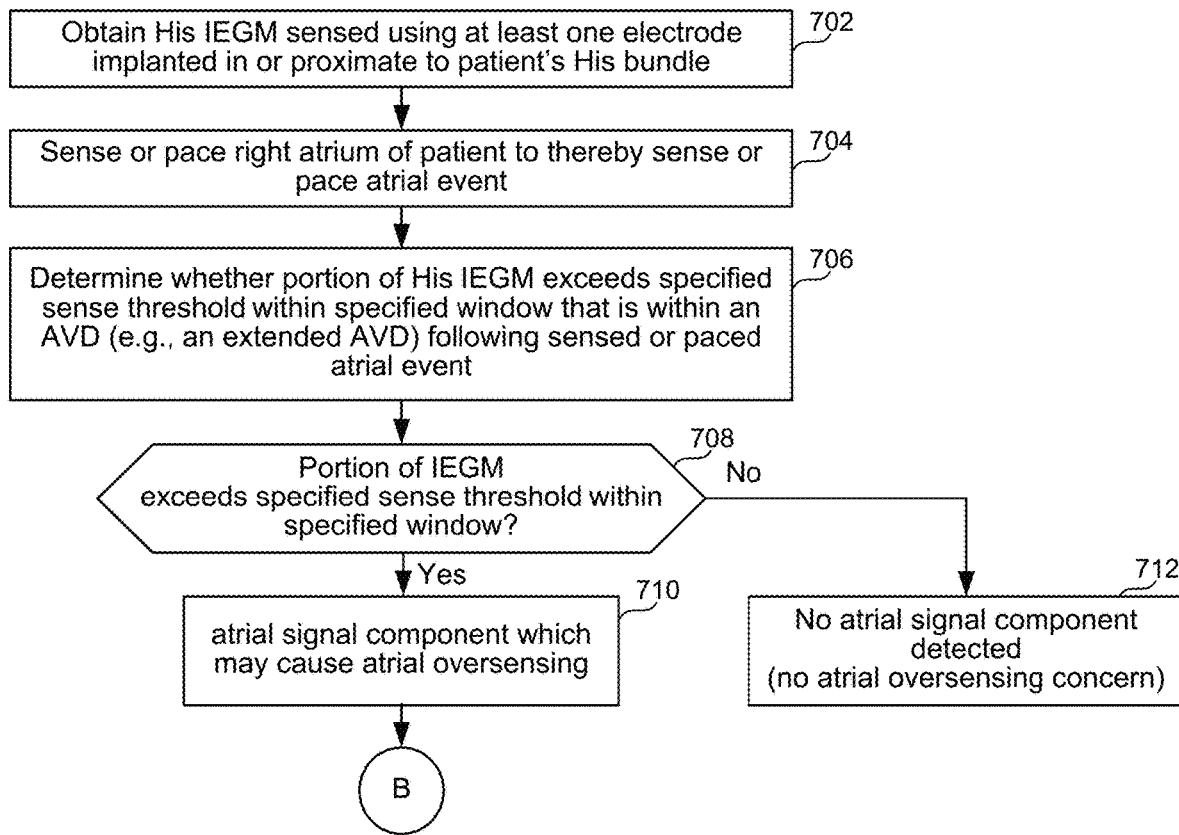
FIGS. 7A and 7B, which can be collectively referred to as FIG. 7, include a high level flow diagram that is used to describe methods for determining whether or not atrial oversensing may occur, and if so, how to characterize potential atrial oversensing and/or reduce the likelihood of atrial oversensing.
Figure 7B:
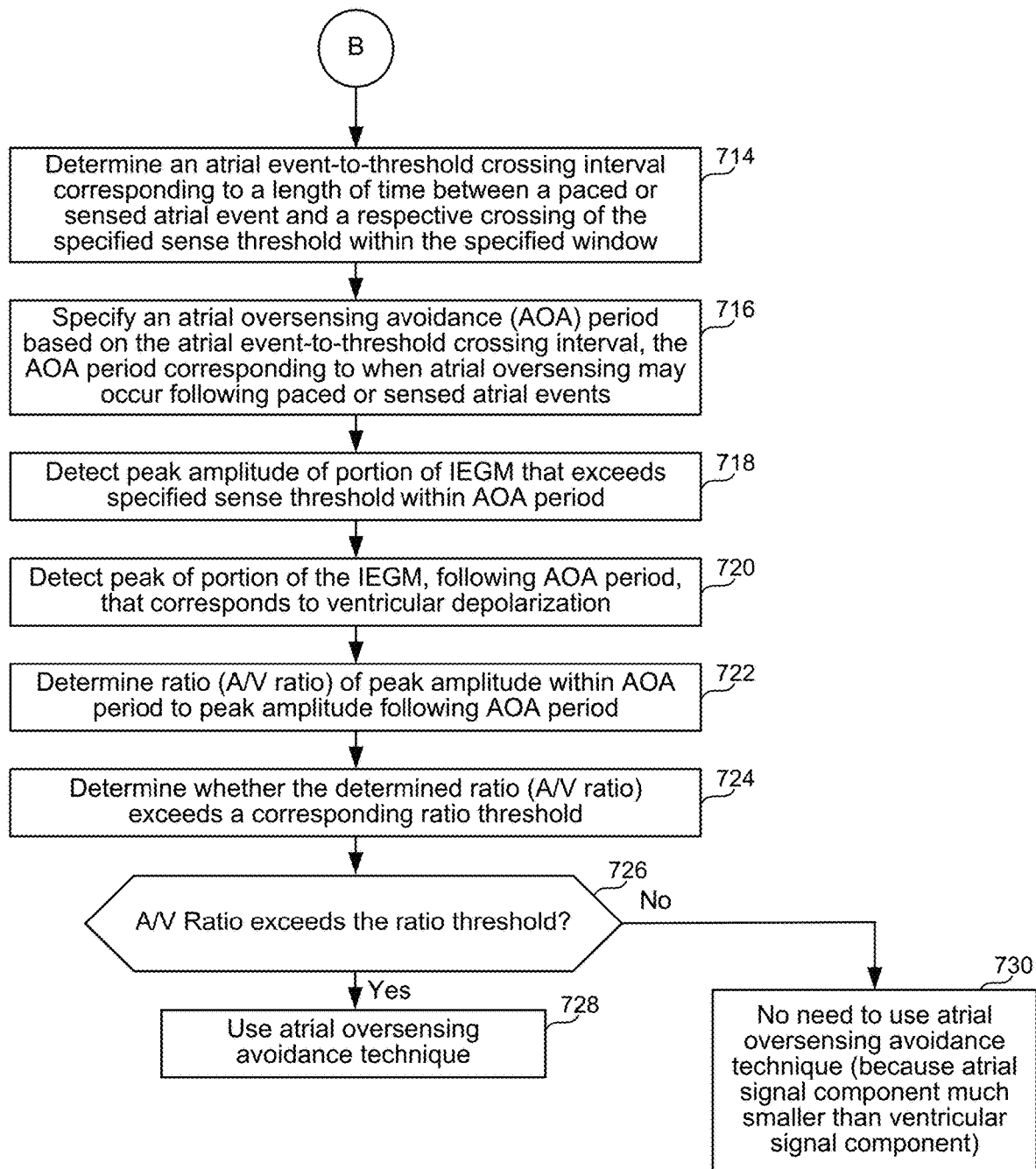

FIGS. 7A and 7B, which can be collectively referred to as FIG. 7, include a high level flow diagram that is used to describe methods for determining whether or not atrial oversensing may occur, and if so, how to characterize the atrial oversensing and/or reduce the likelihood of further atrial oversensing. Such methods can be used with an implantable medical device (e.g., 102 or 202) including one or more electrodes that can be used for sensing and pacing, wherein such a device can make up an entire implantable medical system, or may just be part of (e.g., a subsystem of) an implantable medical system.

Referring to FIG. 7A, step 702 involves obtaining an IEGM sensed using at least one electrode implanted in or proximate to a patient's His bundle. Since the IEGM obtained at step 702 is sensed using at least one electrode implanted in or proximate to a patient's His bundle, such an IEGM can be referred to more specifically as a His IEGM. Step 702 is the same as step 502 described above with reference to FIG. 5, and thus, additional details of step 702 can be appreciated from the above discussion of step 502.

Still referring to FIG. 7A, step 704 involves sensing or pacing a patient's right atrium to thereby sense or pace an atrial event. A paced atrial event can also be referred to as an atrial pace (AP), and a sensed intrinsic atrial event can also be referred to as an atrial sense (AS), as was noted above in the discussion of step 504. Step 704 can be performed, e.g., using at least one of the electrodes of the right atrial lead 120, but is not limited thereto.

Step 706 involves determining whether a portion of the His IEGM exceeds a specified sense threshold within a specified window that is within an AVD following the sensed or paced atrial event. More specifically, the specified window coincides with a portion of the AVD, but is preferably shorter than the AVD. Step 706 can be performed by comparing samples of the His IEGM to the specified sense threshold, to thereby determine whether or not at least one of the samples exceeds the specified sense threshold. In contrast to the AVD referred to in step 506 above, the AVD used at step 706 is preferably an extended AVD that is long enough to allow for intrinsic atrioventricular (AV) conduction within the AVD, in which case this test can be performed while the system/device is in DDD mode. When intrinsic AV conduction is not detected, i.e., no threshold crossing is detected outside of the specified window, a backup pacing pulse should preferably be delivered at the end of the AVD. For an example, the AVD used at step 706 can be set to 350 ms following an atrial paced event (aka AP), or the AVD used at step 706 can be set to 300 ms following an atrial sensed event (aka AS), as noted above. Where the AVD used at step 706 is 350 ms following an AP, then the specified window (within which it is determined whether the His IEGM exceeds the specified sense threshold) can, e.g., correspond to the first 160 ms of the 350 ms AVD. Where the AVD used at step 706 is 300 ms following an AS, then the specified window (within which it is determined whether the His IEGM exceeds the specified sense threshold) can, e.g., correspond to the first 100 ms of the 300 ms AVD. The use of longer or shorter AVD values and window lengths are also possible, and within the scope of the embodiments described herein. If the AVD referred to in step 706 is not long enough to allow for intrinsic AV conduction within the AVD, then the test should be performed while the system/device is in DDT mode, in which case ventricular pacing can be triggered at an end of the AVD. Additionally or alternatively, ventricular pacing can be triggered in response to atrial oversensing being detected, or more specifically, in response to detecting a portion of the His IEGM exceeding the specified sense threshold within the AVD.

Step 708 is a decision block or step, which directs flow to step 710 or to step 724, depending upon the results of step 706. More specifically, at step 708 there is a determination of whether or not there was a determination (at step 706) that a portion of the His IEGM exceeded the specified sense threshold within the specified window. If the answer to the determination at step 708 is No, then flow goes to step 712 and it is concluded that no atrial signal component was detected, and thus, that atrial oversensing is not a concern. However, if the answer to the determination at step 708 is Yes, then flow goes to step 710 and it is concluded that an atrial signal component was detected and that atrial oversensing is possible, and thus, is a potential concern. Following step 710, flow goes to step 714 in FIG. 7B. The steps show in FIG. 7B can be used to characterize potential atrial oversensing and/or reduce the likelihood of further atrial oversensing.

While steps 706 and 708 are shown as two distinct steps in FIG. 7A, these steps can alternatively be combined into a single step, as would be appreciated by one skilled in the art. Flow can go directly from step 710 to step 714, as shown in FIGS. 7A and 7B. Alternatively, in response to detecting an atrial signal component (which may cause oversensing), steps 702-708 can be repeated one or more time(s) to confirm the detection of an atrial signal component within the His IEGM, before flow goes to step 714. In other words, step 714 can be performed in response to detecting an atrial signal component within the His IEGM, or confirmation thereof. Step 714-726 can be performed for or using a same one or more cardiac cycle analyzed at steps 702-710, or for or using one or more cardiac cycles thereafter.

Step 714 involves determining an atrial event-to-threshold crossing interval corresponding to a length of time between a paced or sensed atrial event and a respective crossing of the specified sense threshold within the specified window (that is within the AVD).

Step 716 then involves specifying an atrial oversensing avoidance (AOA) period based on the atrial event-to-threshold crossing interval, wherein the AOA period corresponds to when atrial oversensing may occur following paced or sensed atrial events. Flow then goes to step 718.

Step 718 involves detecting a peak amplitude of the portion of the IEGM that exceeds the specified sense threshold within the AOA period. Step 720 involves detecting a peak of a portion of the IEGM, following the AOA period, that corresponds to a ventricular depolarization. Step 722 involves determining a ratio of the peak amplitude within the AOA period to the peak amplitude following the AOA period (that corresponds to a ventricular depolarization). Since the ratio determine at step 722 is a ratio of the amplitudes of an atrial signal component relative to a ventricular signal component, the ratio can also be referred to more specifically as the A/V ratio. In accordance with certain embodiments, the AOA period can be a period of fixed length that is temporally centered about where the atrial signal component was detected in response to the threshold crossing. It is also possible that the AOA period is rate dependent, such that it is inversely proportional to a patient's heart rate, or is proportion to a patient's VV interval, or the like. It is also possible that the AOA period is not is temporally centered about where the atrial signal component was detected. Other variations are also possible, and within the scope of the embodiments described herein.

At step 724 there is a determination of whether or not the A/V ratio (determined at step 722) exceeds a ratio threshold. Step 726 is a decision block or step, which directs flow to step 728 or to step 730, depending upon the results of step 726. More specifically, at step 726 there is a determination of whether or not there was a determination (at step 724) that the A/V ratio (determined at step 722) exceeds the ratio threshold. If the answer to the determination at step 726 is No, then flow goes to step 730 and it is concluded that there is no need to use an atrial oversensing avoidance technique, since the atrial signal component is relatively small compared to the ventricular signal component, and thus, it is unlikely that an atrial signal component will be mistakenly detected as a ventricular signal component. However, if the answer to the determination at step 728 is Yes, then flow goes to step 728 and it is concluded that an atrial oversensing avoidance technique should be used. In other words, if flow goes to step 728 then atrial oversensing is considered to be a concern. While steps 724 and 726 are shown as two distinct steps in FIG. 7B, these steps can alternatively be combined into a single step, as would be appreciated by one skilled in the art. The same sense threshold that is used within the AOA period (to detect a portion of the IEGM exceeding the sense threshold) can be used to detect a ventricular depolarization following AOA period, or a different threshold can be used, depending upon implementation.

If it is determined at step 728 that atrial oversensing is a potential concern, an alert can be issued to the patient and/or a medical personnel. Additionally, or alternatively, detected atrial signal components can be recorded in a log. If atrial signal components are not detected for at least some length of time, then there may be no need to continue to search for a portion of the IEGM within the AOA period exceeding the specified sense threshold. In other words, a so called AOA technique can be disabled if no atrial signal components are detected, or more generally it atrial oversensing is not determined to be a potential concern.

Figure 8:
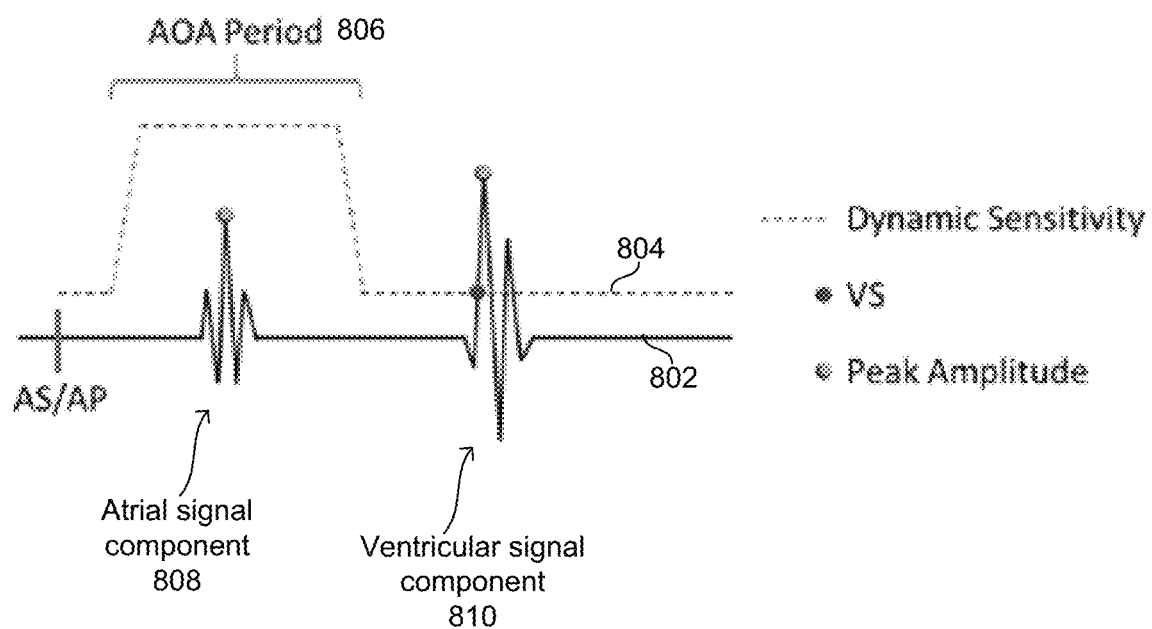
FIG. 8 illustrates a multi-level sense threshold which can be used to avoid atrial oversensing between the time of an atrial sensed event (AS) or atrial paced event (AP) and a following ventricular depolarization represented in a His IEGM, in accordance with certain embodiments of the present technology.

After specifying the AOA period, and while the implantable medical system is in DDD mode, further sensing or pacing of the right atrium of the patient occurs to thereby sense or pace an atrial event. In certain embodiments, in order to avoid further atrial oversensing, a multi-level sense threshold is used to detect ventricular events following sensed or paced atrial events, an example of which is shown in FIG. 8. The use of a multi-level sense threshold is one example of an atrial oversensing avoidance technique that may be used, in response to concluding that atrial oversensing is a potential concern.

Referring to FIG. 8, shown therein is an example His IEGM 802. The dashed line 804 shown in FIG. 8 corresponds to a multi-level sense threshold which can be used to avoid atrial oversensing between the time of an AS or AP and a following ventricular depolarization represented by the ventricular signal component in the His IEGM. As can be appreciated from FIG. 8, the multi-level sense threshold 804 is greater during an AOA period 806 than following the AOA period 806, in order to avoid detecting the atrial signal component 808 during the AOA period 806.

The embodiments summarized with reference to FIGS. 7 and 8 can be used to detect potential atrial oversensing and characterize amplitudes of the atrial and ventricular signal components of a His IEGM. In certain uses of such embodiments, wherein a system/device is in DDD mode with sensed/paced AVD of 300/350 ms (or some other values), the test applies a low sensitivity (high sensing threshold) for a period to purposely avoid sensing the atrial signal component 808 following AS/AP, then reverts to high sensitivity to sense the ventricular signal component 810, as can be appreciated from FIG. 8. The period of low sensitivity is the AOA period 806. The peak amplitude of atrial signal component 808, if present, in the AOA period 806 is compared to the peak amplitude of the ventricular signal component 810. Atrial oversensing can be declared if the A/V ratio is greater than a programmed threshold (e.g. 0.5). The measured atrial and ventricular signal component peak amplitudes can also be used to program a dynamic AOA algorithm, which can use a multi-level sense threshold 804 such as the one shown in FIG. 8.

FIG. 9A includes a table (Table 1) that summarizes stim-to-onset intervals of patient's with and without atrial oversensing, which table can be used to specify the length of the specified window used with the atrial oversensing test summarized with reference to FIGS. 5 and 6. More specifically, based on the analysis of the clinical data shown in FIG. 9A, it was determined that 140 ms is an appropriate length of the specified windows referred to in steps 506, 508, 514, and 516, although the use of shorter and longer windows is also within the scope of the embodiments described herein.

FIG. 9B includes a table (Table 2) that summarizes AS/AP to onset intervals of patient's with and without oversensing, which table can be used to specify the length of the specified window used with the atrial oversensing test summarized with reference to FIG. 7. More specifically, based on the analysis of the clinical data shown in FIG. 9B, it was determined that 100 ms is an appropriate length of the specified windows referred to in steps 706 and 708, although the use of shorter and longer windows is also within the scope of the embodiments described herein.

The embodiments of the present technology described above with reference to FIG. 7 can be used to detect and further characterize atrial oversensing. When implementing such an embodiment, the specified sense threshold that is used (at steps 706 and 708) is preferably relatively low, to provide for high sensitivity. In a specific implementation, the medical device/system that implements such an embodiment is programmed to be in DDT mode, e.g., with a sensed/paced AVD of 150/200 ms. DDT mode ensures ventricular pacing in case of atrial oversensing on the His lead. If sensing occurs on the ventricular channel (VS), the interval from the A sense/pace marker (AS/AP) to signal onset on the His lead is measured. At an example base rate of 60 bpm, the AS/AP to true ventricular sensing should be at least 120 ms and can be much longer in patients with AV block or bundle branch block. Based on analysis of clinical data (summarized in Table 2 of FIG. 9B), an AS/AP to VS interval of less than 100 ms is a reliable indicator of atrial oversensing on the His IEGM. In certain embodiments, the peak amplitude following VS can be measured in the sense refractory period. Both the AS/AP-VS interval and the peak amplitude of the VS can be measured for multiple consecutive beats. If the AS/AP to VS intervals are consistently less than 100 ms (or some other specified temporal threshold), atrial oversensing is confirmed. The AS/AP to VS intervals that are less than 100 ms (or some other specified temporal threshold) can be used to characterize when atrial oversensing could occur. The peak amplitudes of VS events that are within 100 ms (or some other specified temporal threshold) of the AS/AP event can be used to the characterize the amplitude of atrial oversensing. Other variations are also possible, and within the scope of the embodiments described herein.

Atrial Capture Test

Where one or more electrodes (of a His lead or LCP) are implanted within or proximate the His bundle, it is possible that undesirable direct atrial capture may occur in response to HBP pulses being delivered to the His bundle. Certain embodiments of the present technology described below (with reference to FIGS. 10A, 10B, and 11A-11G) relate to determining whether or not such atrial capture occurs. In accordance with certain embodiment, the atrial capture test described with reference to FIGS. 10A, 10B, and 11A-11G can be performed by or under the control of the atrial capture detector 367, or more generally, using one or more processors.

Figure 10A:
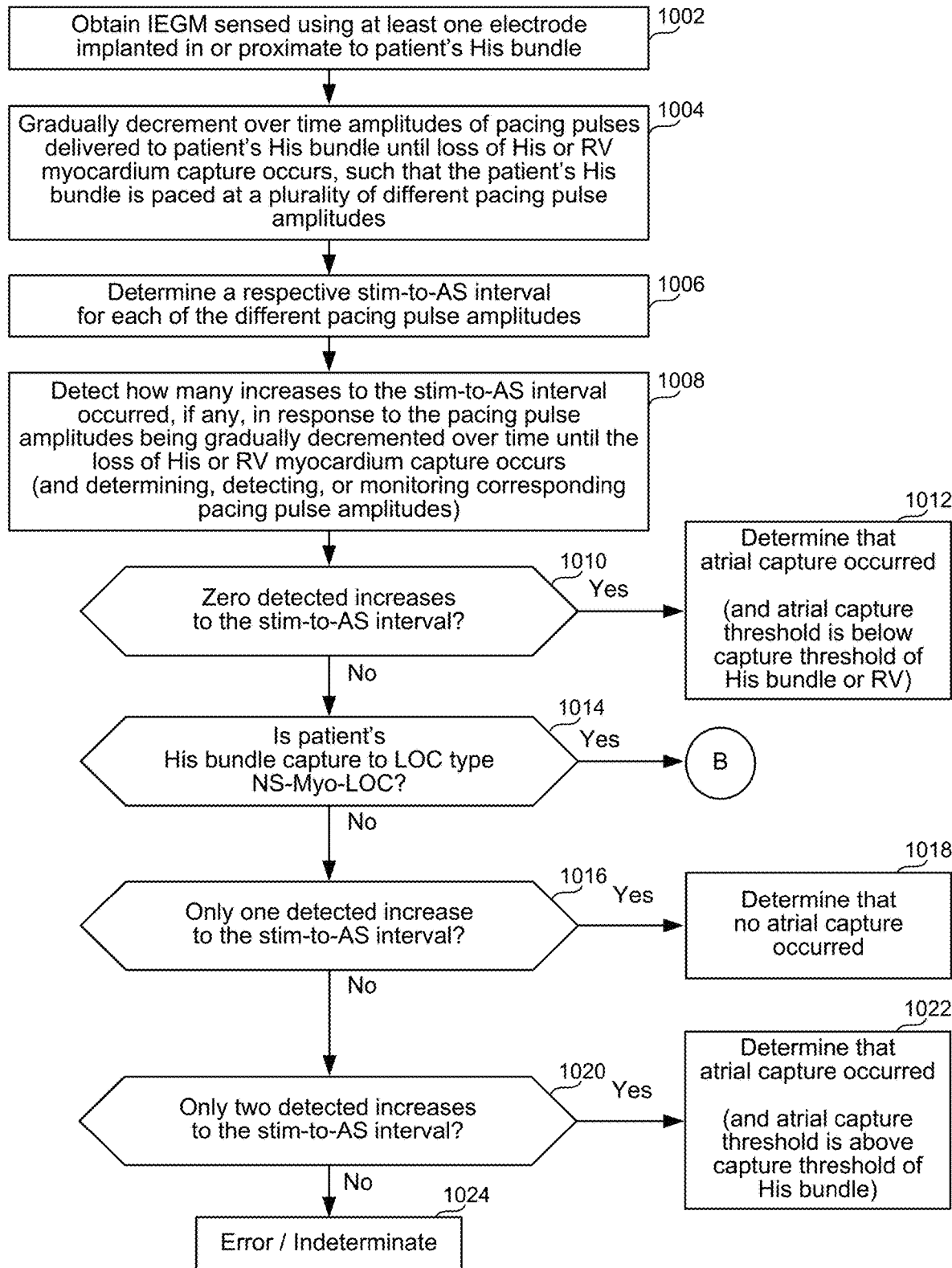
FIGS. 10A and 10B, which can be collectively referred to as FIG. 10, includes a high level flow diagram that is used to describe methods for performing an atrial capture test, in accordance with certain embodiments of the present technology, wherein such a test can be used to detect if and/or when atrial capture occurs in response to HBP.
Figure 10B:
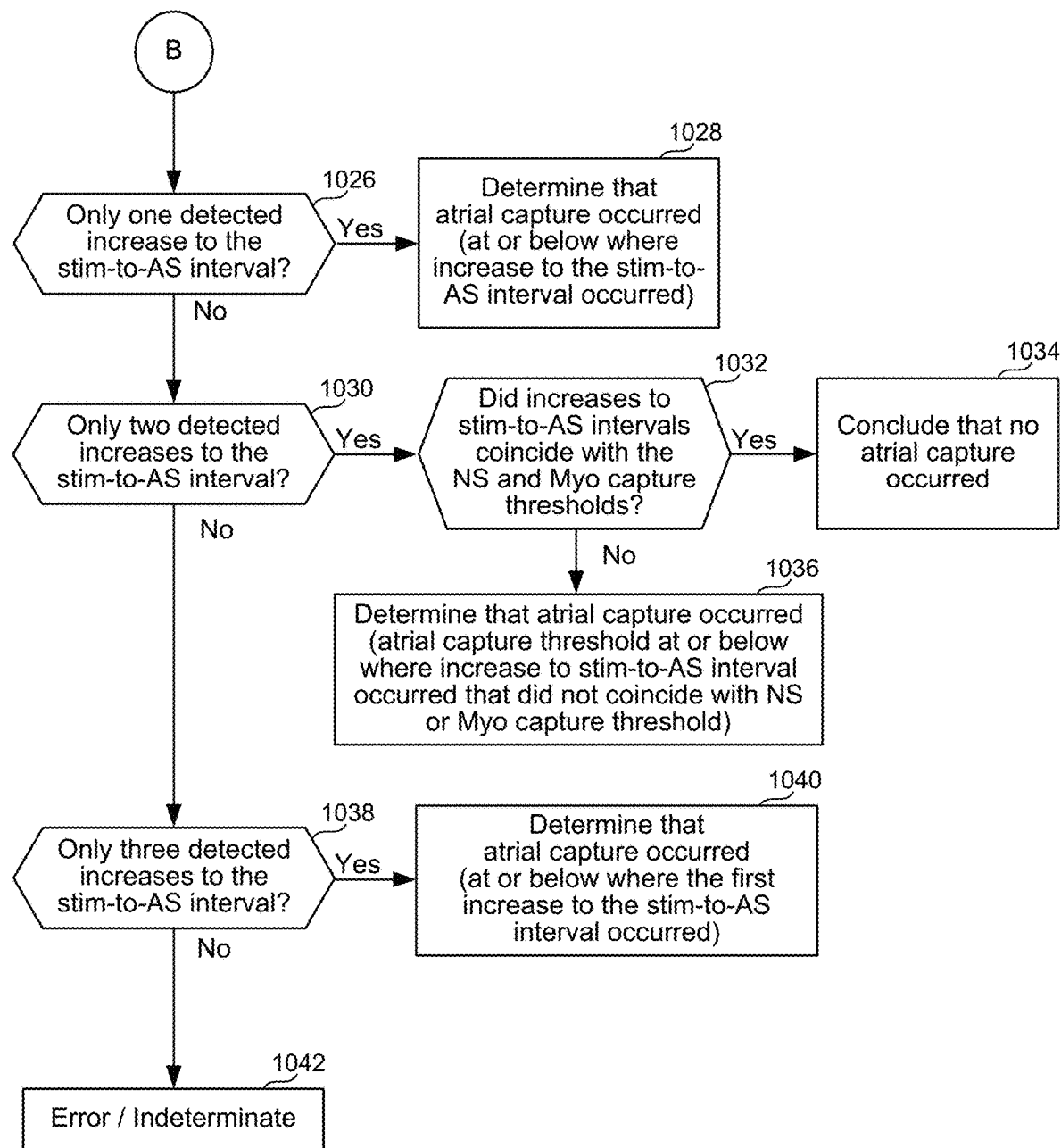

FIGS. 10A and 10B, which can be referred to collectively as FIG. 10, include a high level flow diagram that is used to describe methods for performing an atrial capture test, in accordance with certain embodiments of the present technology. Such a test can be used to detect if and/or when atrial capture occurs in response to pacing a patient's His bundle using at least one electrode that is implanted in or proximate to the patient's His bundle. Preferably, prior to performing the atrial capture test described with reference to FIG. 10, a patient's type of His bundle capture is determined using a His bundle capture threshold test, such as, but not limited to, one described in U.S. Provisional Patent Application No. 62/948,047, titled AUTOMATIC PACING IMPULSE CALIBRATION USING PACING RESPONSE TRANSITIONS filed Dec. 13, 2019, which was incorporated herein by reference above. The His bundle pacing (HBP) capture type exhibited by a patient is dictated by the His bundle anatomy of the patient, His lead/electrode location, and pacing pulse amplitude. The various HBP capture types that may occur include selective His bundle capture (S-HBP), nonselective His bundle capture (NS-HBP), and myocardium only capture (Myo-HBP). The myocardium only capture (Myo-HBP) type of His bundle pacing can also be represented using the nomenclature M-HPB. A patient having an implanted lead/electrode used to perform HBP can experience one of the following five different responses to amplitudes of HBP pulses being gradually decremented over time until loss of capture (LOC) of the His or RV myocardium occurs: (1) S-HBP to LOC; (2) NS-HBP to LOC; (3) Myo-HBP to LOC; (4) NS-HBP to S-HBP to LOC; or (5) NS-HBP to Myo-HBP to LOC. Such gradually decrementing over time of HBP pulses until LOC of the His or RV myocardium occurs can be performed as part of a His bundle capture threshold test, which may or may not be automated, depending upon the specific implementation. The above listed five different responses can also be referred to as His capture to LOC types.

Referring to FIG. 10, step 1002 involves obtaining an IEGM sensed using at least one electrode implanted in or proximate to a patient's His bundle. Since the IEGM obtained at step 1002 is sensed using at least one electrode implanted in or proximate to a patient's His bundle, such an IEGM can be referred to more specifically as a His IEGM. Step 1002 is the same as step 502 described above with reference to FIG. 5, and thus, additional details of step 1002 can be appreciated from the above discussion of step 502. Still referring to FIG. 7A, step 1004 involves, during a plurality of cardiac cycles during which pacing of a patient's His bundle occurs, using at least one electrode implanted in or proximate to a patient's His bundle to deliver pacing pulses to the patient's His bundle, wherein the amplitudes of the pacing pulses are gradually decremented over time until there is loss of capture of the His bundle or RV myocardium. In other words, step 1004 involves gradually decremented over time amplitudes of pacing pulses that are delivered to the patient's His bundle until loss of His or RV myocardium capture occurs, such that the patient's His bundle is paced at a plurality of different pacing pulse amplitudes.

Step referring to FIG. 10, step 1006 involves, for each pacing pulse amplitude, of the different pacing pulse amplitudes used during the pacing of the patient's His bundle, determining a respective stimulation-to-atrial sense (stim-to-AS) interval corresponding to a length of time between when a His pacing pulse having the pacing pulse amplitude is delivered and when a respective atrial sensed event occurs. Step 1008 involves detecting how many increases to the stim-to-AS interval occurred, if any, in response to the pacing pulse amplitudes being gradually decremented over time until the loss of His or RV myocardium capture occurs. Since patients will likely have some natural variation to their stim-to-AS intervals, an increase to the stim-to-AS interval will only be considered to have occurred (at step 1008) if the increase is significant, e.g., by at least some specified meaningful amount (e.g., 25 ms) or by at least some specified meaningful percentage (e.g., 25%), which can be predetermined or programmable. Step 1008 can also involve determining, detecting, or monitoring corresponding pacing pulse amplitudes, for reasons explained below. The remaining steps which are described in further detail below, are used to determine whether atrial capture occurred, during the pacing of the patient's His bundle, based on results of the detecting how many increases to the stim-to-AS interval occurred, if any.

At step 1010 there is a determination of whether zero detected increases to the stim-to-AS interval occurred (i.e., whether no increases to the stim-to-AS interval were detected). If the answer to the determination at step 1010 is Yes, then flow goes to step 1012, and it is concluded that atrial capture occurred, and that the atrial capture threshold is below the capture threshold of the His bundle. In other words, steps 1010 and 1012 involve determining that atrial capture occurred if there were zero detected increases to the stim-to-AS interval in response to the pacing pulse amplitudes being gradually decremented over time until the loss of His or RV myocardium capture occurs. If the answer to the determination at step 1010 is No, then flow goes to step 1014.

At step 1014 there is a determination of whether the specific patient (for which the atrial capture test is being performed) has the specific His bundle capture to LOC type NS-HBP to Myo-HBP to LOC, which can also be referred to more succinctly as NS-Myo-LOC. Such a patient will experience nonselective (NS) His bundle capture at relatively high HBP pulse amplitudes, myocardium only capture (Myo-HBP) at somewhat lower HBP pulse amplitudes, and then eventual complete loss of capture (LOC) of the His bundle and RV at even lower HBP pulse amplitudes. This is a special case type of patient, for which the steps described in FIG. 10B should be performed (instead of the steps 1016-1024 in FIG. 10A). For patient's having one of the other four types of His bundle to LOC capture types, including: S-HBP to LOC (which can also be referred to more succinctly as S-LOC); NS-HBP to LOC (which can also be referred to more succinctly as (NS-LOC); Myo-HBP to LOC (which can also be referred to more succinctly as Myo-LOC); and NS-HBP to S-HBP to LOC (which can also be referred to more succinctly as NS-S-LOC), flow should go directly from step 1014 to step 1016. For this discussion, initially it will be assumed that the answer to step 1010 is No, and that flow goes to step 1016.

At step 1016 there is a determination of whether there was only one detected increase to the stim-to-AS interval that occurred (in response to the pacing pulse amplitudes being gradually decremented over time until the loss of His or RV myocardium capture occurred). If the answer to the determination at step 1015 is Yes, then flow goes to step 1018, and it is concluded that no atrial capture occurred. In other words, steps 1016 and 1018 involve determining that no atrial capture occurred if there was only one detected increase to the stim-to-AS interval in response to the pacing pulse amplitudes being gradually decremented over time until the loss of His or RV myocardium capture occurs. If the answer to the determination at step 1016 is No, then flow goes to step 1020.

At step 1020 there is a determination of whether there were exactly two detected increase to the stim-to-AS interval that occurred (in response to the pacing pulse amplitudes being gradually decremented over time until the loss of His or RV myocardium capture occurred). If the answer to the determination at step 1020 is Yes, then flow goes to step 1022, and it is concluded that atrial capture occurred, and that the atrial capture threshold is above the capture threshold of the His bundle. In other words, steps 1020 and 1022 involve determining that atrial capture occurred if there were exactly two detected increases to the stim-to-AS interval in response to the pacing pulse amplitudes being gradually decremented over time until the loss of His or RV myocardium capture occurs. If the answer to step 1020 is No, which should only occur where there are three or more increases to the stim-to-AS interval (in response to the pacing pulse amplitudes being gradually decremented over time until the loss of His or RV myocardium capture occurs), this will be treated as an error (since that should not occur) and the results of the atrial capture test will be considered indeterminate, as detected at step 1024.

Returning to step 1014, if the answer to step 1014 was Yes, meaning the His capture to LOC type of the patient is NS-Myo-LOC, then flow goes to step 1026 in FIG. 10B. At step 1026 in FIG. 10B there is a determination of whether there was only one detected increase to the stim-to-AS interval that occurred. If the answer to the determination at step 1026 is Yes, then flow goes to step 1028, and it is concluded that atrial capture occurred, and that the atrial capture threshold is at or below the pulse amplitude at where the one stim-to-AS interval occurred. In other words, steps 1026 and 1028 involve determining that atrial capture occurred (in a patient have an NS-Myo-LOC His capture to LOC type) if there was only one detected increase to the stim-to-AS interval in response to the pacing pulse amplitudes being gradually decremented over time until the loss of His or RV myocardium capture occurs. If the answer to the determination at step 1026 is No, then flow goes to step 1030.

At step 1030 there is a determination of whether there were exactly two detected increases to the stim-to-AS intervals that occurred (in response to the pacing pulse amplitudes being gradually decremented over time until the loss of His or RV myocardium capture occurred). If the answer to the determination at step 1030 is Yes, then flow goes to step 1032. At step 1032 there is a determination of whether the two increases to the stim-to-AS intervals coincided with the patient's NS capture threshold and the patient's Myo capture threshold. If the answer to the determination at step 1032 is Yes, then it is concluded that no atrial capture occurred, as shown at step 1034. Rather, it is concluded that the first increase to the stim-to-AS interval was caused by a transition from NS-to-Myo capture, and the second increase to the stim-to-AS interval was caused by the transition from Myo-to-LOC.

If the answer to the determination at step 1032 is No, then flow goes to step 1036. At step 1036 it is concluded that atrial capture occurred, and that the atrial capture threshold is at or below where the increase to the stim-to-AS interval did not coincide with the NS capture threshold or the Myo capture threshold.

Returning to step 1030, if the answer to the determination at step 1030 was No, then flow goes to step 1038. At step 1038 there is a determination of whether exactly three increases to the stim-to-AS intervals occurred (in response to the pacing pulse amplitudes being gradually decremented over time until the loss of His or RV myocardium capture occurred). If the answer to the determination at step 1038 is Yes, then flow goes to step 1040. At step 1040 it is concluded that atrial capture occurred, and that the atrial capture threshold is at or below where the first increase to the stim-to-AS interval occurred.

If the answer to the determination at step 1038 is No, which should only occur where there are four or more increases to the stim-to-AS interval (in response to the pacing pulse amplitudes being gradually decremented over time until the loss of His or RV myocardium capture occurs), this will be treated as an error (since that should not occur) and the results of the atrial capture test will be considered indeterminate, as indicated at step 1042

Figure 11A:
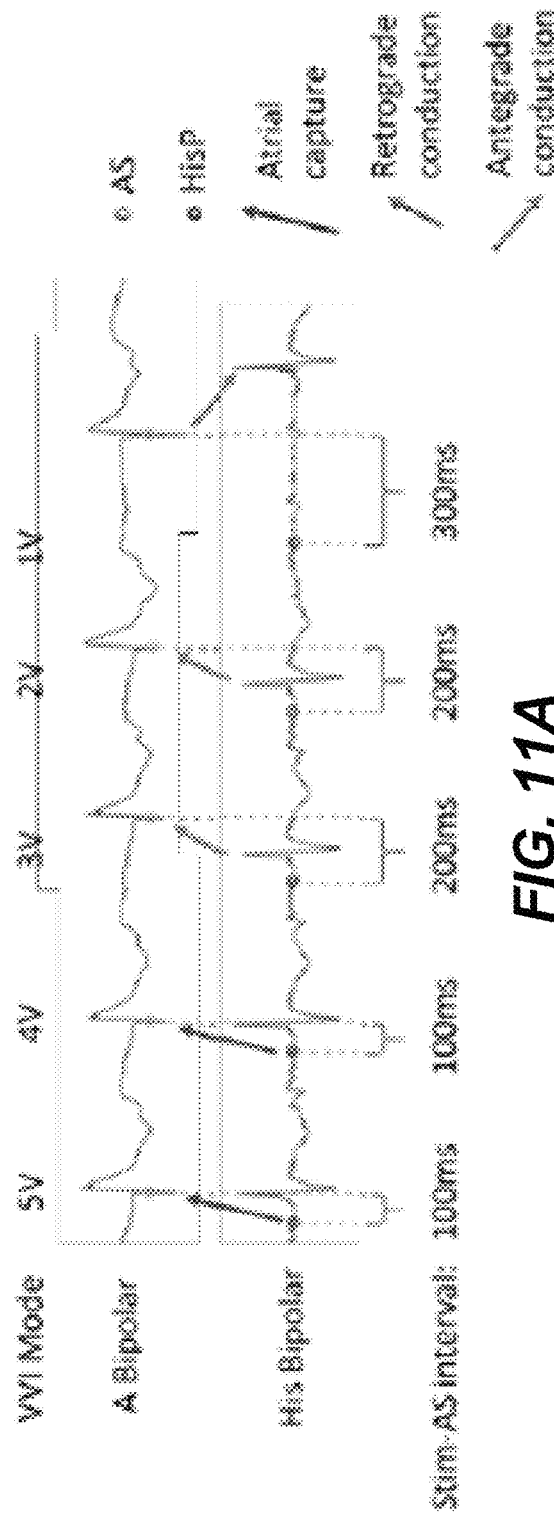
FIGS. 11A-11G each include an example atrial bipolar IEGM and an example His bipolar IEGM that are used to show how the atrial capture test, which is described with reference to the high level flow diagram of FIG. 10, can be used to detect whether atrial capture occurs in response to HBP, as well as to provide other types of determinations.

FIG. 11A, which includes an example of an atrial bipolar IEGM (A Bipolar) and a corresponding example His bipolar IEGM (His Bipolar) for a patient having one of the other four His bundle capture to LOC types, besides the NS-Myo-LOC type. FIG. 11A shows that the amplitudes of His bundle pacing (HBP) pulses are gradually decremented from 5V, to 4V, to 3V, to 2V, to 1V, and that loss of capture (LOC) of the His bundle or RV occurred at 1V. FIG. 11A also shows that in response to the gradual decrementing of the amplitudes of the HBP pulses, the stim-to-AS interval increased twice, including from 100 ms to 200 ms, and then from 200 ms to 300 ms. Because there were exactly two increases to the stim-AS interval (in response to the pacing pulse amplitudes being gradually decremented over time until the loss of His or RV myocardium capture occurs), at steps 1020 and 1022 of FIG. 10A, it would be determined that atrial capture occurred and that the atrial capture threshold is above the His bundle capture threshold.

Figure 11B:
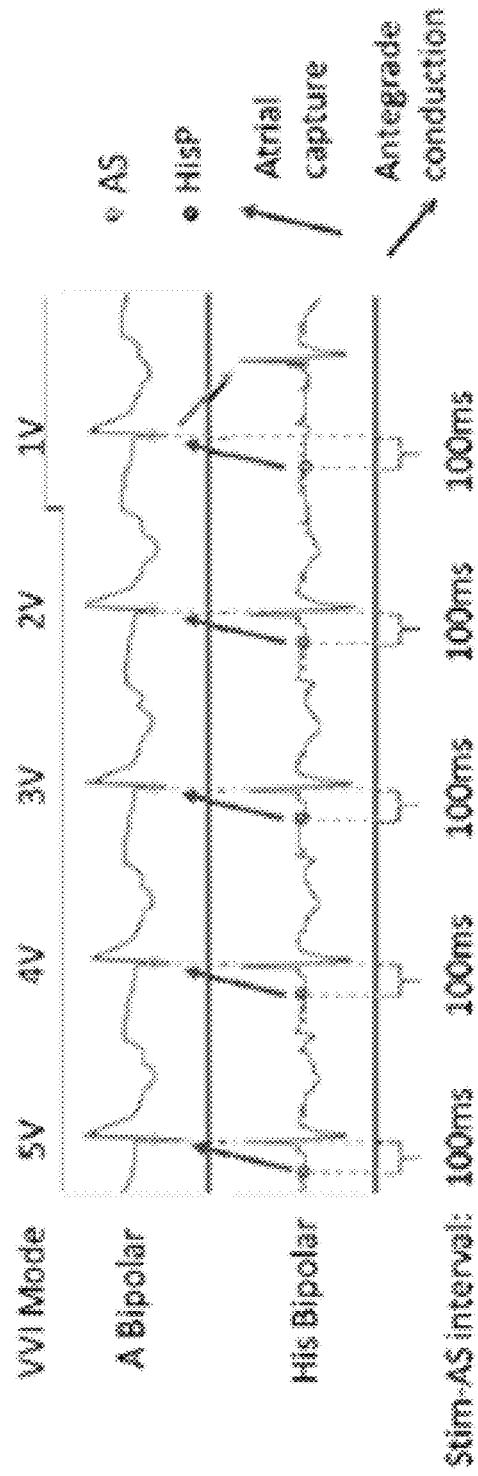

FIG. 11B includes a further example of an atrial bipolar IEGM (A Bipolar) and a corresponding example His bipolar IEGM (His Bipolar) for a patient having one of the other four His bundle capture to LOC types, besides the NS-Myo-LOC His capture type. FIG. 11B, which includes an example atrial bipolar IEGM (A Bipolar) and a corresponding example His bipolar IEGM (His Bipolar), is used to show another example of how the atrial capture test described with reference to FIG. 10 can be used to determine whether atrial capture was detected. FIG. 11B shows that the amplitudes of HBP pulses are gradually decremented from 5V, to 4V, to 3V, to 2V, to 1V, and that LOC of the His bundle or RV occurred at 1V. FIG. 11B also shows that in response to the gradual decrementing of the amplitudes of the HBP pulses, the stim-to-AS interval never increased, but rather, remained at 100 ms. In other words, FIG. 11B shows zero increases to the stim-to-AS interval. Because there were zero increases to the stim-AS interval (in response to the pacing pulse amplitudes being gradually decremented over time until the loss of His or RV myocardium capture occurs), at steps 1010 and 1012 of FIG. 10A, it would be determined that atrial capture occurred and that the atrial capture threshold is below the His bundle capture threshold.

FIG. 11C-11G include examples of atrial bipolar IEGMs (A Bipolar) and corresponding examples His bipolar IEGMs (His Bipolar) for patients specifically having the NS-Myo-LOC His capture to LOC type. Each of these FIGS. shows that there is a transition from NS-HBP to Myo-HBP at 3V, and that LOC occurs at 1V.

Figure 11C:
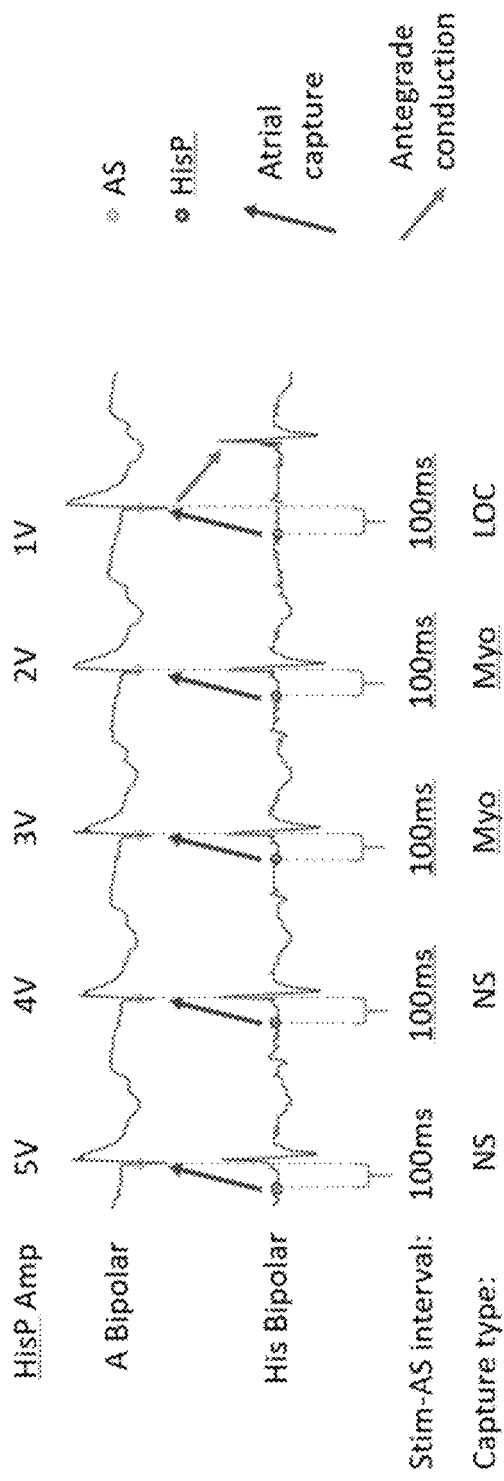

In FIG. 11C there are zero increases to the stim-to-AS interval shown. Because there were zero increases to the stim-AS interval (in response to the pacing pulse amplitudes being gradually decremented over time until the loss of His or RV myocardium capture occurs), at steps 1010 and 1012 of FIG. 10A, it would be determined that atrial capture occurred, and that the atrial capture threshold is below the His bundle capture threshold.

Figure 11D:
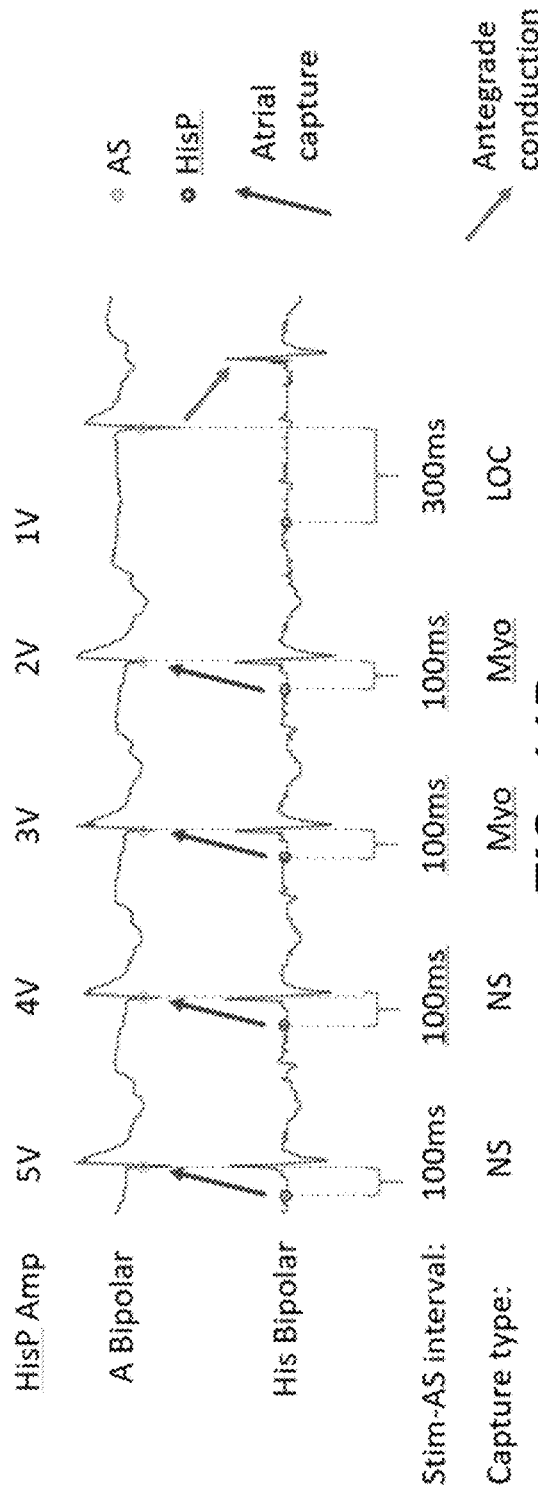

In FIG. 11D there is exactly one increase to the stim-to-AS interval shown. Because there was exactly one increase to the stim-AS interval (in response to the pacing pulse amplitudes being gradually decremented over time until the loss of His or RV myocardium capture occurs), and the patient has the NS-Myo-LOC His capture to LOC type, at steps 1026 and 1028 in FIG. 10B it would be determined that atrial capture occurred, and that the atrial capture threshold is at are below where the increase to the stim-to-AS interval occurred (i.e., at 1V or below).

Figure 11E:
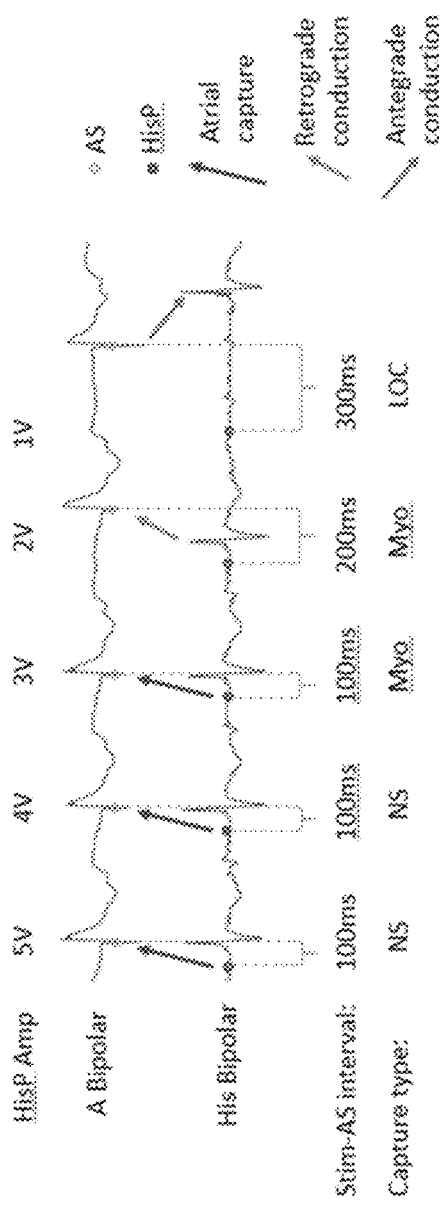

In FIG. 11E there are exactly two increases to the stim-to-AS interval shown, from 100 ms to 200 ms, and from 200 ms to 300 ms. Since the stim-to-AS interval increase from 100 ms to 200 ms did not occur at one of the NS or Myo capture thresholds, and the patient has the NS-Myo-LOC His capture type, at steps 1030, 1032 and 1036 in FIG. 10B it would be determined that atrial capture occurred, and that the atrial capture threshold is at are below where the increase to the stim-to-AS interval occurred that did no coincide with the NS or Myo threshold (i.e., at 3V or within the range of 2V to 3V).

Figure 11F:
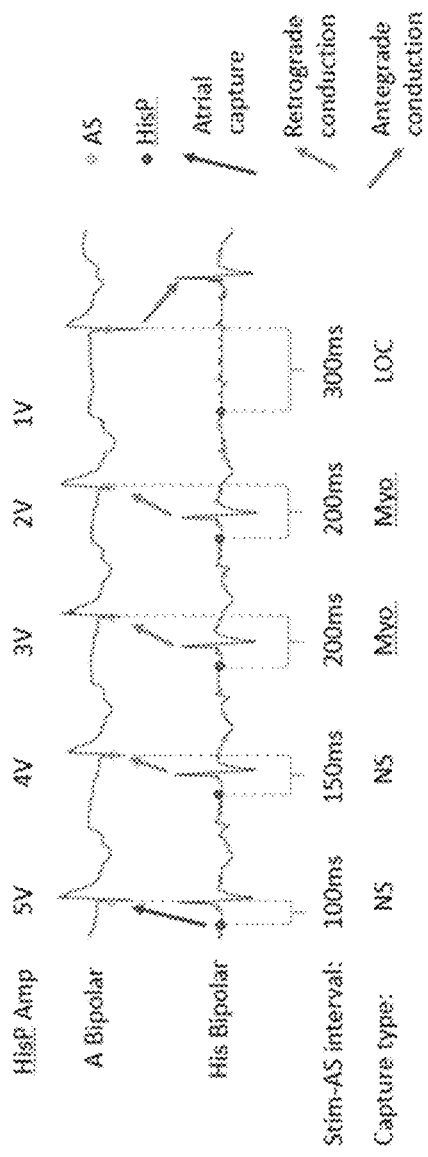

In FIG. 11F there are exactly three increases to the stim-to-AS interval shown, from 100 ms to 150 ms, from 150 ms to 200 ms, and from 200 ms to 300 ms. Because there were exactly three increases to the stim-AS interval (in response to the pacing pulse amplitudes being gradually decremented over time until the loss of His or RV myocardium capture occurs), and the patient has the NS-Myo-LOC His capture to LOC type, at steps 1038 and 1040 of FIG. 10B, it would be determined that atrial capture occurred, and that the atrial capture threshold is at or below where the first increase to the stim-to-AS interval occurred (i.e., at 5V or within the range of 4V to 5V).

Figure 11G:
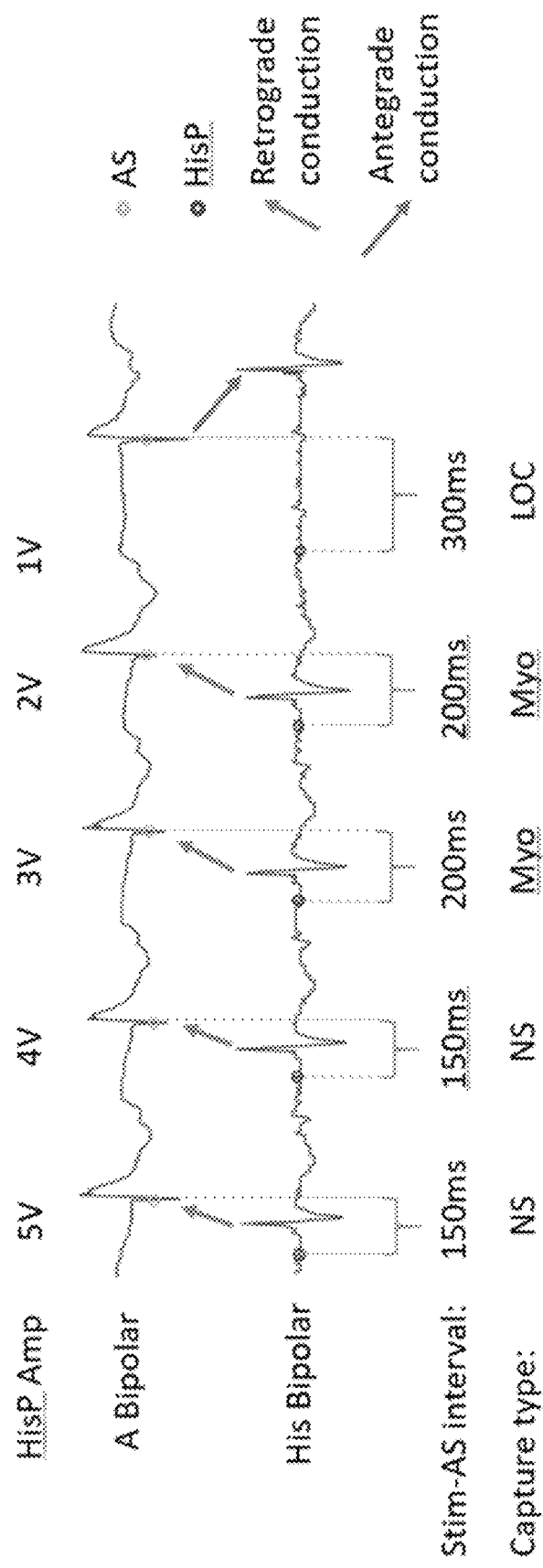

In FIG. 11G there are exactly two increases to the stim-to-AS interval shown, from 150 ms to 200 ms, and from 200 ms to 300 ms. In FIG. 11G, the two increases to the stim-to-AS interval coincided with the NS and Myo capture thresholds, i.e., the increase from 150 ms to 200 ms coincided with the NS capture threshold, and the increase from 200 ms to 300 ms coincided with the Myo capture threshold. Accordingly, it would be determined at step 1030, 1032, and 1034 in FIG. 10B that atrial capture did not occur.

Certain embodiments described with reference to FIGS. 10A, 10B and 11A-11G take advantage of the fact that capture of the His bundle in NS capture results in a shorter retrograde conduction time compared to Myo capture. Such embodiments also take advantage of the fact that in the absence of atrial capture, the Stim-AS interval measures the retrograde conduction and should increase only when the loss of His capture occurs. Therefore, a sudden increase in the Stim-AS interval at the transition for NS capture to Myo capture should not trigger an atrial capture detection.

AV Node Capture Test

Due to the close proximity of the His bundle to the AV node, it would be beneficial to check if a His lead/electrode being implanted is undesirable in or contacting the AV node, before completing an implant procedure. Because of the slow conduction through the AV node, AV node pacing may result in long stim-onset interval (e.g., greater than 140 ms) in the absence of atrial oversensing. An AV node capture test, according to certain embodiments of the present technology, is described below with reference to the high level flow diagram of FIG. 12, as well as with reference to FIG. 13. In accordance with certain embodiment, the AV node capture testing described with reference to FIGS. 12 and 13 can be performed by or under the control of the AV node capture detector 368, or more generally, using one or more processors.

Figure 12:
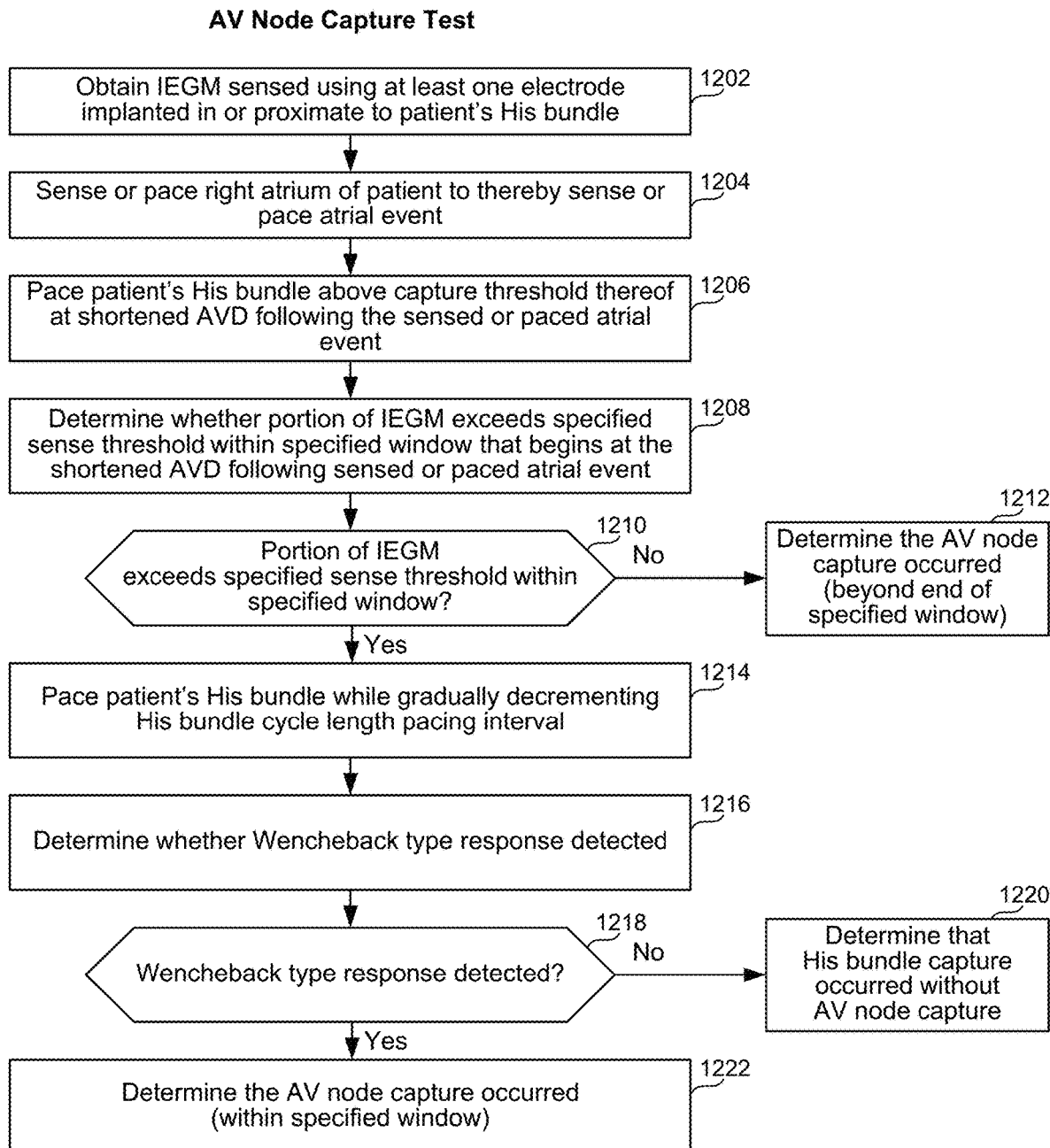
FIG. 12 includes a high level flow diagram that is used to describe certain methods for determining whether or not AV node capture occurs in response to HBP.

Referring to FIG. 12, step 1202 involves obtaining an intracardiac electrogram (IEGM) sensed using at least one electrode implanted in or proximate to a patient's His bundle. Since the IEGM obtained at step 1202 is sensed using at least one electrode implanted in or proximate to a patient's His bundle, such an IEGM can be referred to more specifically as a His IEGM. Step 1202 is the same as step 502 described above with reference to FIG. 5, and thus, additional details of step 1202 can be appreciated from the above discussion of step 502. Still referring to FIG. 12 step 1204 involves, for each of a plurality of cardiac cycles during which the IEGM is obtained, sensing or pacing a right atrium of the patient to thereby sense or pace an atrial event. Step 1206 involves, pacing the patient's His bundle at a shortened AVD following the sensed or paced atrial event. Step 1208 involves determining whether a portion of the IEGM exceeds a specified sense threshold within a specified window that begins the shortened AVD following the sensed or paced atrial event.

Step 1210 is a decision block or step, which directs flow to step 1212 or to step 1214, depending upon the results of step 1208. More specifically, at step 1210 there is a determination of whether or not there was a determination (at step 1208) that a portion of the His IEGM exceeded the specified sense threshold within the specified window. If the answer to the determination at step 1210 is No, then flow goes to step 1212 and it is concluded that AV node capture occurred. However, if the answer to the determination at step 1210 is Yes, then flow goes to step 1214. While steps 1208 and 1210 are shown as two distinct steps in FIG. 12, these steps can alternatively be combined into a single step, as would be appreciated by one skilled in the art.

Step 1214 involves pacing the patient's His bundle while gradually decrementing the His bundle cycle length pacing interval. In other words, at step 1214 the interval from one HBP pulse to the next is gradually decremented over time.

Step 1216 involves determining whether a Wenchebach type response is detected (in response to pacing the patient's His bundle while gradually decrementing the His bundle cycle length pacing interval, at step 1214). Step 1218 is a decision block or step, which directs flow to step 1220 or to step 1222, depending upon the results of step 1216. More specifically, at step 1218 there is a determination of whether or not there was a determination (at step 1216) that the Wenchebach type response was detected. If the answer to the determination at step 1218 is No, then flow goes to step 1220 and it is concluded that His bundle capture occurred without AV node capture. However, if the answer to the determination at step 1218 is Yes, then flow goes to step 1222, and it is concluded that AV node capture occurred. While steps 1216 and 1218 are shown as two distinct steps in FIG. 12, these steps can alternatively be combined into a single step, as would be appreciated by one skilled in the art.

The Wenchebach type response (which is related to the Wenchebach Phenomenon) can be detected by determining whether stimulation-to-onset (stim-to-onset) intervals progressively increased in response to the gradually decrementing over time the His bundle cycle length pacing interval. The Wenchebach type response (which is indicative of AV node capture) is detected if it is determined that the stimulation-to-onset intervals progressively increased in response to the gradually decrementing over time the His bundle cycle length pacing interval. Conversely, the Wenchebach type response is not detected if the stimulation-to-onset intervals remain consistent (i.e., substantially the same length) in response to the gradually decrementing over time the His bundle cycle length pacing interval.

In accordance with certain embodiments, the AV node capture test described with reference to FIG. 12 is performed when the system/device is in DDD mode, and HBP is performing using a paced/sensed AVD of 50/25 ms (i.e., 50 ms following an AP, or 25 ms following an AS). During such HBP the amplitude of the HBP pulses should be sufficiently high to ensure His capture. Further, in certain embodiments, the stim-onset intervals are measured withing search windows of 140 ms from His pacing. If no evoked response is detected for any of the beats, the test would declare AV node capture. Otherwise, if every beat has a stim-onset interval of less than 140 ms, a decremental cycle length pacing test will be performed to check for the Wenckebach phenomenon, which is unique to the AV node. In the case of AV node capture, the stim-onset interval would progressively prolong with decreasing pacing cycle length till eventually loss of capture occurs. Whereas in the case of His capture (without AV node capture), the stim-onset interval would remain consistent till loss of capture of the His bundle occurs when the pacing cycle length reaches the His effective refractory period.

Figure 13A:
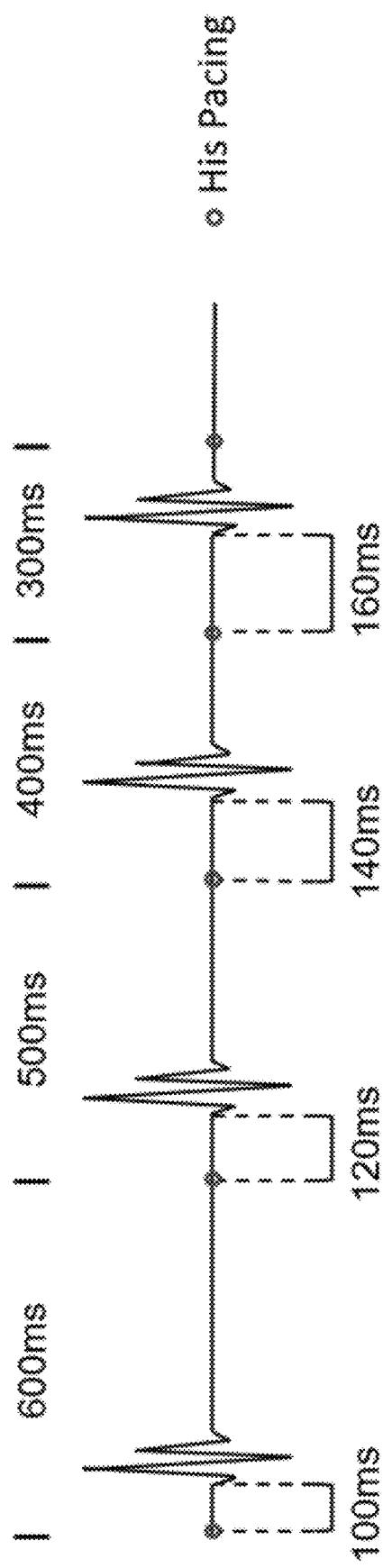
FIGS. 13A and 13B, which can be collectively referred to as FIG. 13, shows examples His IEGMs that are used to explain how the methods described with reference to the flow diagram of FIG. 12 can be used to determine whether or not AV node capture occurs in response to HBP.
Figure 13B:
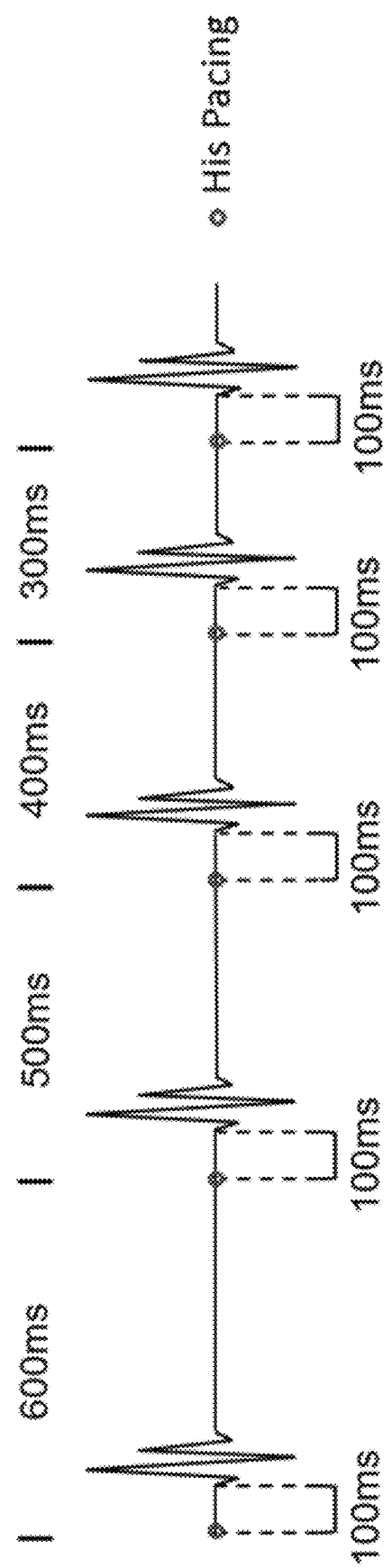

FIGS. 13A and 13B are used to show two different possible responses that may occur in response to the pacing performed at step 1214, i.e., to pacing the patient's His bundle while gradually decrementing the His bundle cycle length pacing interval. In FIG. 13A the His bundle cycle length pacing intervals are shown as being decreased from 600 ms, to 500 ms, to 400 ms, to 300 ms, and the respective stim-to-onset intervals are shown as increasing from 100 ms, to 120 ms, to 140 ms, to 160 ms, which corresponds to a Wenchebach type response. Accordingly, if the response shown in FIG. 13A were detected in response to the His bundle cycle length pacing intervals being gradually decreased, then the AV capture node test would conclude the AV node capture occurred.

In FIG. 13B the His bundle cycle length pacing intervals are again shown as being decreased from 600 ms, to 500 ms, to 400 ms, to 300 ms. However, in contrast to FIG. 13A, in FIG. 13B the respective stim-to-onset intervals are shown as remaining consistently at 100 ms, which does not correspond to a Wenchebach type response. Accordingly, if the response shown in FIG. 13B were detected in response to the His bundle cycle length pacing intervals being gradually decreased, then the AV node capture test would conclude the His bundle capture occurred without AV node capture.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed embodiments. For example, it would be possible to combine or separate some of the steps shown in various flow diagrams shown in FIGS. 5, 7, 10 and/or 12. For another example, it is possible to change the boundaries of some of the blocks shown in FIG. 3.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A medical system configured to selectively perform His capture management, the system comprising:
   one or more implantable electrodes that can be used for sensing and pacing;
   a sensing circuit configured to sense a His intracardiac electrogram (IEGM) using at least one of the one or more implantable electrodes configured to be implanted in or proximate to a patient's His bundle;
   a pulse generator configured to selectively produce pacing pulses that are to be delivered to the patient's His bundle using the at least one of the one or more implantable electrodes configured to be implanted in or proximate to the patient's His bundle; and
   a controller configured to
      cause pacing of the patient's right atrium using at least one of the one or more implantable electrodes configured to be implanted in the patient's right atrium to thereby cause a paced atrial event;
      determine whether a portion of the His IEGM exceeds a specified sense threshold within a specified window that begins at an end of an atrioventricular delay (AVD) following the paced atrial event;
      detect atrial oversensing based on results of the determining whether the portion of the His IEGM exceeds the specified sense threshold within the specified window;
      prevent performance of the His capture management in response to the atrial oversensing being detected; and
      after the atrial oversensing has been detected, at a later point in time that the atrial oversensing is no longer detected, cause the His capture management to be performed, which includes causing pacing of the patient's His bundle, using the at least one of the one or more implantable electrodes configured to be implanted in or proximate to the patient's His bundle, and determine a capture threshold associated with the patient's His bundle.

2. The system of claim 1, wherein:
   the specified window, which begins at the end of the AVD following the paced atrial event, comprises an evoked response window; and
   the controller, in order to determine whether the portion of the His IEGM exceeds the specified sense threshold within the specified window that begins at the end of the AVD following the paced atrial event, is configured to
      at the end of the AVD following the paced atrial event, trigger the evoked response window by causing delivery of a subthreshold pacing pulse to the patient's His bundle using the at least one of the one or more implantable electrodes configured to be implanted in or proximate to the patient's His bundle, the subthreshold pacing pulse having energy below a previously determined capture threshold associated with the patient's His bundle.

3. The system of claim 1, wherein the controller is configured to:
   determine a first onset interval corresponding to a length of time between a beginning of the specified window and when the portion of the His IEGM exceeds the specified sense threshold within the specified window;
   cause further pacing of the patient's right atrium to thereby cause a further paced atrial event;
   determine whether a further portion of the His IEGM exceeds the specified sense threshold within a further specified window that begins at an end of an extended AVD following the further paced atrial event, wherein the extended AVD is equal to the AVD plus an extension interval that is less than the first onset interval;
   determine a second onset interval corresponding to a length of time between a beginning of the further specified window and when the further portion of the His IEGM within the further specified window exceeds the specified sense threshold;
   determine whether the second onset interval is equal to the first onset interval minus the extension interval; and
   detect the atrial oversensing in response to determining that the second onset interval is equal to the first onset interval minus the extension interval.

4. The system of claim 3, wherein:
   the specified window comprises an evoked response window;
   the controller, in order to determine whether the portion of the His IEGM exceeds the specified sense threshold within the specified window, is configured to
      at the end of the AVD following the paced atrial event, trigger the evoked response window by causing delivery of a subthreshold pacing pulse to the patient's His bundle using the at least one of the one or more implantable electrodes configured to be implanted in or proximate to the patient's His bundle, the subthreshold pacing pulse having energy below a previously determined capture threshold associated with the patient's His bundle;
   the further specified window comprises a further evoked response window; and
   the controller, in order to determine whether the further portion of the His IEGM exceeds the specified sense threshold within the further specified window, is configured to
      at the end of the extended AVD following the further paced atrial event, trigger the further evoked response window by causing delivery of a further subthreshold pacing pulse to the patient's His bundle using the at least one of the one or more implantable electrodes configured to be implanted in or proximate to the patient's His bundle.

5. A medical system, comprising:
   one or more implantable electrodes that can be used for sensing and pacing;
   a sensing circuit configured to sense a His intracardiac electrogram (IEGM) using at least one of the one or more implantable electrodes configured to be implanted in or proximate to a patient's His bundle;
   one or more pulse generators configured to
      selectively produce one or more pacing pulses that are to be delivered to the patient's His bundle using at least one of the one or more implantable electrodes configured to be implanted in or proximate to the patient's His bundle; and
      selectively produce one or more ventricular pacing pulses that are to be delivered to the patient's right ventricle using at least one of the one or more implantable electrodes configured to be implanted in the patient's right ventricle; and a controller configured to
cause sensing or pacing of the patient's right atrium to thereby sense or pace an atrial event;
determine whether a portion of the His IEGM exceeds a specified sense threshold within a specified window within an atrioventricular delay (AVD) following the sensed or paced atrial event;
detect an atrial signal component within the His IEGM based on whether it is determined that the portion of the His IEGM exceeds the specified sense threshold within the specified window within the AVD, wherein detection of the atrial signal component within the His IEGM is indicative of potential atrial oversensing; and
trigger ventricular pacing in response to the portion of the His IEGM exceeding the specified sense threshold within the AVD, or trigger ventricular pacing at an end of the AVD in response to no portion of the His IEGM exceeding the specified sense threshold within the AVD;
wherein the AVD comprises an extended AVD that is long enough to allow for intrinsic atrioventricular (AV) conduction within the AVD.

6. The system of claim 5, wherein the controller is configured to:
determine an atrial event-to-threshold crossing interval corresponding to a length of time between the paced or sensed atrial event and a respective crossing of the specified sense threshold within the specified window within the AVD;
specify an atrial oversensing avoidance (AOA) period based on the atrial event-to-threshold crossing interval, the AOA period corresponding to when atrial oversensing may occur following paced or sensed atrial events;
detect a peak amplitude of the portion of the His IEGM that exceeds the specified sense threshold within the AOA period;
detect a peak amplitude of a further portion of the His IEGM, following the AOA period, that corresponds to a ventricular depolarization;
determine a ratio of the peak amplitude within the AOA period to the peak amplitude following the AOA period;
determine whether the determined ratio exceeds a specified ratio threshold; and
determine that an atrial oversensing avoidance technique is to be used in response to determining that the determined ratio exceeds the specified ratio threshold.

7. The system of claim 6, wherein the controller is further configured to:
cause sensing or pacing of the right atrium of the patient to thereby sense or pace a further atrial event; and
determine whether another portion of the His IEGM exceeds a multi-level sense threshold within a specified window that begins following the further sensed or paced atrial event;
wherein the multi-level sense threshold is greater during each said AOA period than following each said AOA period.

8. A method for use with an implantable medical system configured to selectively perform His capture management, the method comprising:

obtaining a His intracardiac electrogram (His IEGM) sensed using at least one electrode implanted in or proximate to a patient's His bundle;
pacing the patient's right atrium using at least one electrode implanted in the patient's right atrium to thereby cause a paced atrial event;
determining whether a portion of the His IEGM exceeds a specified sense threshold within a specified window that begins at an end of an atrioventricular delay (AVD) following the paced atrial event;
detecting atrial oversensing based on results of the determining whether the portion of the His IEGM exceeds the specified sense threshold within the specified window;
preventing performance of the His capture management in response to detecting the atrial oversensing; and
after detecting the atrial oversensing, at a later point in time that the atrial oversensing is no longer detected, performing the His capture management, which includes pacing of the patient's His bundle, using the at least one electrode implanted in or proximate to the patient's His bundle, and determining a capture threshold associated with the patient's His bundle.

9. The method of claim 8, wherein:
the specified window, which begins at the end of the AVD following the paced atrial event, comprises an evoked response window; and
the determining whether the portion of the His IEGM exceeds the specified sense threshold within the specified window includes
at the end of the AVD following the paced atrial event, triggering the evoked response window by delivering a subthreshold pacing pulse to the patient's His bundle using the at least one electrode that is implanted in or proximate to the patient's His bundle, the subthreshold pacing pulse having energy below a previously determined capture threshold associated with the patient's His bundle.

10. The method of claim 8, further comprising:
determining a first onset interval corresponding to a length of time between a beginning of the specified window and when the portion of the His IEGM exceeds the specified sense threshold within the specified window;
further pacing the patient's right atrium to thereby cause a further paced atrial event;
determining whether a further portion of the His IEGM exceeds the specified sense threshold within a further specified window that begins at an end of an extended AVD following the further paced atrial event, wherein the extended AVD is equal to the AVD plus an extension interval that is less than the first onset interval;
determining a second onset interval corresponding to a length of time between a beginning of the further specified window and when the further portion of the His IEGM within the further specified window exceeds the specified sense threshold;
determining whether the second onset interval is equal to the first onset interval minus the extension interval; and
detecting the atrial oversensing in response to determining that the second onset interval is equal to the first onset interval minus the extension interval.

11. The method of claim 10, wherein:
the specified window comprises an evoked response window;

the determining whether the portion of the His IEGM exceeds the specified sense threshold within the specified window includes,
at the end of the AVD following the paced atrial event, triggering the evoked response window by delivering a subthreshold pacing pulse to the patient's His bundle using the at least one electrode implanted in or proximate to the patient's His bundle, the subthreshold pacing pulse having energy below a previously determined capture threshold associated with the patient's His bundle;
the further specified window comprises a further evoked response window; and
the determining whether the further portion of the His IEGM exceeds the specified sense threshold within the further specified window includes,
at the end of the extended AVD following the further paced atrial event, triggering the further evoked response window by delivering a further subthreshold pacing pulse to the patient's His bundle using the at least one electrode implanted in or proximate to the patient's His bundle.

12. A method for use with an implantable medical system, the method comprising:
obtaining a His intracardiac electrogram (His IEGM) sensed using at least one electrode implanted in or proximate to a patient's His bundle;
sensing or pacing a right atrium of the patient to thereby sense or pace an atrial event;
determining whether a portion of the His IEGM exceeds a specified sense threshold within a specified window within an atrioventricular delay (AVD) following the sensed or paced atrial event; and
detecting an atrial signal component within the His IEGM based on results of the determining whether the portion of the His IEGM exceeds the specified sense threshold within the specified window within the AVD, wherein the detecting the atrial signal component within the His IEGM is indicative of potential atrial oversensing; and
triggering ventricular pacing in response to detecting the portion of the His IEGM exceeding the specified sense threshold within the AVD;
wherein the method is performed while the implantable medical system is in one of DDT or DDD mode.

13. The method of claim 12, further comprising, in response to detecting the atrial signal component within the His IEGM, repeating the obtaining, the sensing or pacing, and the determining one or more times to confirm the detecting of the atrial signal component within the His IEGM.

14. A method for use with an implantable medical system, the method comprising:
obtaining a His intracardiac electrogram (His IEGM) sensed using at least one electrode implanted in or proximate to a patient's His bundle;
sensing or pacing a right atrium of the patient to thereby sense or pace an atrial event;
determining whether a portion of the His IEGM exceeds a specified sense threshold within a specified window within an atrioventricular delay (AVD) following the sensed or paced atrial event; and
detecting an atrial signal component within the His IEGM based on results of the determining whether the portion of the His IEGM exceeds the specified sense threshold within the specified window within the AVD, wherein the detecting the atrial signal component within the His IEGM is indicative of potential atrial oversensing; and
triggering ventricular pacing in response to detecting the portion of the His IEGM exceeding the specified sense threshold within the AVD;
wherein the AVD is long enough to allow for intrinsic atrioventricular conduction within the AVD.

15. A method for use with an implantable medical system, the method comprising:
obtaining a His intracardiac electrogram (His IEGM) sensed using at least one electrode implanted in or proximate to a patient's His bundle;
sensing or pacing the patient's right atrium to thereby sense or pace an atrial event;
determining whether a portion of the His IEGM exceeds a specified sense threshold within a specified window within an atrioventricular delay (AVD) following the sensed or paced atrial event; and
triggering ventricular pacing at an end of the AVD in response to no portion of the His IEGM exceeding the specified sense threshold within the AVD;
wherein the method is performed while the implantable medical system is in one of DDT or DDD mode.

16. A method for use with an implantable medical system, the method comprising:
obtaining a His intracardiac electrogram (His IEGM) sensed using at least one electrode implanted in or proximate to a patient's His bundle;
sensing or pacing a right atrium of the patient to thereby sense or pace an atrial event;
determining whether a portion of the His IEGM exceeds a specified sense threshold within a specified window within an atrioventricular delay (AVD) following the sensed or paced atrial event; and
detecting an atrial signal component within the His IEGM based on results of the determining whether the portion of the His IEGM exceeds the specified sense threshold within the specified window within the AVD, wherein the detecting the atrial signal component within the His IEGM is indicative of potential atrial oversensing;
triggering ventricular pacing in response to detecting the portion of the His IEGM exceeding the specified sense threshold within the AVD;
determining an atrial event-to-threshold crossing interval corresponding to a length of time between the paced or sensed atrial event and a respective crossing of the specified sense threshold; and
specifying an atrial oversensing avoidance (AOA) period based on the atrial event-to-threshold crossing interval, the AOA period corresponding to when atrial oversensing may occur following further paced or sensed atrial events.

17. The method of claim 16, further comprising, after specifying the AOA period:
determining that a further portion of the His IEGM within the AOA period exceeds the specified sense threshold,
detecting a peak amplitude of the further portion of the His IEGM that exceeds the specified sense threshold within the AOA period;
detecting a peak amplitude of another portion of the His IEGM, following the AOA period, that corresponds to a ventricular depolarization;
determining a ratio of the peak amplitude within the AOA period to the peak amplitude following the AOA period;
determining whether the determined ratio exceeds a specified ratio threshold; and determining that an atrial oversensing avoidance technique is to be used in response to determining that the determined ratio exceeds the specified ratio threshold.

18. The method of claim 16, further comprising, after specifying the AOA period, and while the implantable medical system is in DDD mode:
further sensing or pacing the right atrium of the patient to thereby sense or pace a further atrial event; and
determining whether an addition portion of the His IEGM exceeds a multi-level sense threshold within a specified window that begins following the further sensed or paced atrial event;
wherein the multi-level sense threshold is greater during each said AOA period than following each said AOA period.

* * * * *